(12) United States Patent
Toledano et al.

(10) Patent No.: US 9,868,103 B2
(45) Date of Patent: Jan. 16, 2018

(54) METAL OXIDE COATING OF WATER INSOLUBLE INGREDIENTS

(75) Inventors: Ofer Toledano, Kfar Saba (IL); Hanan Sertchook, Gedera (IL); Natalia Loboda, Jerusalem (IL); Haim Bar-Simantov, Modiin (IL)

(73) Assignee: SOL-GEL TECHNOLOGIES LTD., Ness Ziona (IL)

(*) Notice: Subject to any disclaimer, the term of this patent is extended or adjusted under 35 U.S.C. 154(b) by 737 days.

(21) Appl. No.: 11/997,823

(22) PCT Filed: Aug. 2, 2006

(86) PCT No.: PCT/IL2006/000892
§ 371 (c)(1),
(2), (4) Date: Sep. 9, 2008

(87) PCT Pub. No.: WO2007/015243
PCT Pub. Date: Feb. 8, 2007

(65) Prior Publication Data
US 2009/0081262 A1  Mar. 26, 2009

Related U.S. Application Data

(60) Provisional application No. 60/704,455, filed on Aug. 2, 2005.

(51) Int. Cl.
| | |
|---|---|
| *A01N 25/28* | (2006.01) |
| *A01N 31/00* | (2006.01) |
| *A01N 47/10* | (2006.01) |
| *A01N 53/02* | (2006.01) |
| *A01N 57/00* | (2006.01) |
| *A01P 13/00* | (2006.01) |
| *A01P 3/00* | (2006.01) |
| *A01P 7/00* | (2006.01) |
| *A61K 31/12* | (2006.01) |
| *A61K 31/203* | (2006.01) |
| *A61K 31/66* | (2006.01) |
| *A61K 8/02* | (2006.01) |
| *A61K 9/50* | (2006.01) |
| *B01J 13/22* | (2006.01) |
| *A01N 25/26* | (2006.01) |
| *A61K 8/11* | (2006.01) |
| *A61K 9/16* | (2006.01) |
| *A61Q 19/00* | (2006.01) |
| *B01J 13/02* | (2006.01) |

(52) U.S. Cl.
CPC .............. *B01J 13/22* (2013.01); *A01N 25/26* (2013.01); *A61K 8/11* (2013.01); *A61K 9/1676* (2013.01); *A61K 9/5078* (2013.01); *A61Q 19/00* (2013.01); *B01J 13/02* (2013.01); *A61K 2800/412* (2013.01); *A61K 2800/434* (2013.01); *A61K 2800/57* (2013.01)

(58) Field of Classification Search
None
See application file for complete search history.

(56) References Cited

U.S. PATENT DOCUMENTS

| | | | |
|---|---|---|---|
| 1,387,107 A | 8/1921 | Carr | |
| 1,671,956 A | 5/1928 | McGregor et al. | |
| 2,885,366 A * | 5/1959 | Iler .......................... | B22F 1/02 |
| | | | 106/38.3 |
| 3,785,798 A | 1/1974 | Horai et al. | |
| 3,826,670 A | 7/1974 | Rees et al. | |
| 3,957,971 A | 5/1976 | Oleniacz | |
| 4,129,645 A | 12/1978 | Barnett et al. | |
| 4,169,069 A | 9/1979 | Unger et al. | |
| 4,349,456 A | 9/1982 | Sowmann | |
| 4,350,681 A | 9/1982 | Fulton, Jr. | |
| 4,361,584 A | 11/1982 | Fulton, Jr. | |

(Continued)

FOREIGN PATENT DOCUMENTS

| | | |
|---|---|---|
| AU | 764016 B2 | 5/2000 |
| AU | 199963469 B2 | 8/2003 |

(Continued)

OTHER PUBLICATIONS

Bugosh, JPhysChem, 65, 1961.*
Tissot, Macromolecules, 34, 2001.*
Wang, Journal of the American Ceramic Society, 85, 8, 2004.*
Skapin, Journal of Colloid and Interface Science, 272, 2004.*
Zhu-Zhu Li et al., Fabrication of Porous Hollow Silica Nanoparticles and Their Applications in Drug Release Control, Journal of Controlled Release 98, 2004, pp. 245-254.
M. Aizawa et al., "Preparation of Spherical Hydrous Silica Oxide Particles under Acidic Condition via Sol-Gel Processing", Journal of Sol-Gel Science and Technology 19, 329-332, 2000.
C. J. Brinker et al., "The Physics and Chemistry of Sol-Gel Processing", Sol-Gel Science, pp. 562-563, May 1990.
P. Bugnon, "Surface treatment of pigments Treatment with inorganic materials", Progress in Organic Coatings 29 (1996) 39-43.
M. A. Butler et al., "An emulsion method for producing fine low density, high surface area silica powder from alkoxides", Journal of Materials Science 31 (1996) 1675-1680.

(Continued)

*Primary Examiner* — Robert A Wax
*Assistant Examiner* — William Craigo
(74) *Attorney, Agent, or Firm* — Mark S. Cohen; Pearl Cohen Zedek Latzer Baratz LLP

(57) ABSTRACT

The invention relates to process for coating a solid, water-insoluble particulate matter, with a metal oxide comprising: (a) contacting the solid water-insoluble particulate matter with a cationic additive in an aqueous medium to obtain a dispersion of said particulate matter having a positive zeta potential; (b) coating the solid water-insoluble particulate matter by precipitation of a metal oxide salt onto the surface of the particulate matter, forming a metal oxide layer thereon; and (c) aging said coating layer. The invention further relates to coated particulate matter obtained by the process and to compositions comprising solid, water-insoluble particulate matter, coated by a metal oxide layer, the particulate matter being a dermatological active agent or a pesticide. The invention additionally relates to methods of treating a surface condition in a subject using compositions comprising solid, water insoluble dermatologically active agent, coated by a metal oxide layer.

47 Claims, 2 Drawing Sheets

(56) References Cited

U.S. PATENT DOCUMENTS

| | | |
|---|---|---|
| 4,387,107 A | 6/1983 | Klein et al. |
| 4,444,746 A | 4/1984 | Harvey et al. |
| 4,464,317 A | 8/1984 | Thies et al. |
| 4,497,794 A | 2/1985 | Klein et al. |
| 4,606,913 A | 8/1986 | Aronson et al. |
| 4,671,956 A | 6/1987 | Bouillon et al. |
| 4,686,211 A | 8/1987 | Hara et al. |
| 4,690,825 A | 9/1987 | Won |
| 4,692,329 A | 9/1987 | Klein et al. |
| 4,769,080 A | 9/1988 | Clark et al. |
| 4,891,211 A | 1/1990 | Winston |
| 4,931,362 A | 6/1990 | Zsifkovits et al. |
| 4,960,772 A | 10/1990 | Sebag et al. |
| 4,988,744 A | 1/1991 | Yamamoto |
| 5,086,075 A | 2/1992 | De Villez |
| 5,126,915 A | 6/1992 | Pepin et al. |
| 5,145,675 A | 9/1992 | Won et al. |
| 5,165,914 A | 11/1992 | Vlock |
| 5,200,334 A | 4/1993 | Dunn et al. |
| 5,223,250 A | 6/1993 | Mitchell et al. |
| 5,269,840 A | 12/1993 | Morris et al. |
| 5,292,801 A | 3/1994 | Avnir et al. |
| 5,387,622 A | 2/1995 | Yamamoto |
| 5,446,028 A | 8/1995 | Klein et al. |
| 5,455,048 A | 10/1995 | Lahmani et al. |
| 5,466,446 A | 11/1995 | Stiefel et al. |
| 5,472,491 A * | 12/1995 | Duschek et al. ............ 106/418 |
| 5,500,223 A | 3/1996 | Behan et al. |
| 5,520,917 A | 5/1996 | Mizuguchi et al. |
| 5,556,617 A | 9/1996 | Ribier et al. |
| 5,587,170 A | 12/1996 | Caisey et al. |
| 5,591,453 A | 1/1997 | Ducheyne et al. |
| 5,607,664 A | 3/1997 | Ascione et al. |
| 5,632,996 A | 5/1997 | Ramirez et al. |
| 5,635,809 A | 6/1997 | Ganser et al. |
| 5,650,311 A | 7/1997 | Avnir et al. |
| 5,670,209 A | 9/1997 | Wyckoff |
| 5,672,301 A | 9/1997 | Orly et al. |
| 5,691,060 A | 11/1997 | Levy et al. |
| 5,700,451 A | 12/1997 | Yue et al. |
| 5,733,531 A | 3/1998 | Mitchnick et al. |
| 5,739,020 A | 4/1998 | Pope |
| 5,767,098 A | 6/1998 | Klein et al. |
| 5,785,977 A | 7/1998 | Breithbarth |
| 5,792,250 A * | 8/1998 | Braun et al. ............ 106/459 |
| 5,851,538 A | 12/1998 | Froix et al. |
| 5,874,105 A | 2/1999 | Watkins et al. |
| 5,876,699 A | 3/1999 | DiSomma et al. |
| 5,879,716 A | 3/1999 | Katz et al. |
| 5,895,757 A | 4/1999 | Pope |
| 5,906,811 A | 5/1999 | Hersh |
| 5,912,016 A | 6/1999 | Perrier et al. |
| 5,914,101 A * | 6/1999 | Tapley et al. ............ 424/59 |
| 5,914,104 A | 6/1999 | Moore |
| 5,932,228 A | 8/1999 | Hall et al. |
| 5,955,109 A | 9/1999 | Won et al. |
| 5,962,517 A | 10/1999 | Murad |
| 5,998,392 A | 12/1999 | Simard et al. |
| 6,013,637 A | 1/2000 | Klein et al. |
| 6,015,548 A | 1/2000 | Siddiqui et al. |
| 6,074,629 A | 6/2000 | Kostinko et al. |
| 6,077,522 A | 6/2000 | Scher et al. |
| 6,090,399 A | 7/2000 | Ghosh et al. |
| 6,096,765 A | 8/2000 | Bershad |
| 6,103,267 A | 8/2000 | Mitchnick et al. |
| 6,117,843 A | 9/2000 | Baroody et al. |
| 6,132,773 A | 10/2000 | Amiche |
| 6,143,280 A | 11/2000 | Pike et al. |
| 6,146,664 A | 11/2000 | Siddiqui |
| 6,159,453 A | 12/2000 | Avnir et al. |
| 6,171,600 B1 | 1/2001 | Dahms |
| 6,197,757 B1 | 3/2001 | Perrier et al. |
| 6,200,375 B1 * | 3/2001 | Guez et al. ............ 106/438 |
| 6,217,852 B1 | 4/2001 | Gildenberg et al. |
| 6,238,650 B1 | 5/2001 | Lapidot et al. |
| 6,242,099 B1 | 6/2001 | Grandmontagne et al. |
| 6,251,313 B1 | 6/2001 | Deubzer et al. |
| 6,280,746 B1 | 8/2001 | Arquette et al. |
| 6,303,149 B1 | 10/2001 | Magdassi et al. |
| 6,303,290 B1 | 10/2001 | Liu et al. |
| 6,337,089 B1 | 1/2002 | Yoshioka et al. |
| 6,436,375 B1 | 8/2002 | Lapidot et al. |
| 6,468,509 B2 | 10/2002 | Lapidot et al. |
| 6,479,146 B1 | 11/2002 | Caruso et al. |
| 6,495,352 B1 | 12/2002 | Brinker et al. |
| 6,534,044 B1 * | 3/2003 | Wada et al. ............ 424/59 |
| 6,537,583 B1 | 3/2003 | Dupuis et al. |
| 6,607,713 B1 | 8/2003 | Chodorowski et al. |
| 6,616,947 B1 | 9/2003 | Depuis |
| 6,703,032 B2 | 3/2004 | Gers-Barlag et al. |
| 6,855,335 B2 | 2/2005 | Seok et al. |
| 6,875,264 B2 | 4/2005 | Zimmermann et al. |
| 6,913,825 B2 | 7/2005 | Ostafin et al. |
| 7,001,592 B1 | 2/2006 | Traynor et al. |
| 7,037,513 B1 | 5/2006 | Traynor et al. |
| 7,052,913 B2 | 5/2006 | Babich et al. |
| 7,758,888 B2 | 7/2010 | Lapidot |
| 8,039,020 B2 | 10/2011 | Lapidot et al. |
| 7,758,888 C1 | 11/2011 | Lapidot |
| 2002/0064541 A1 * | 5/2002 | Lapidot et al. ............ 424/401 |
| 2002/0151527 A1 | 10/2002 | Wiegand et al. |
| 2002/0193321 A1 | 12/2002 | Vishnupad et al. |
| 2003/0004118 A1 | 1/2003 | Vishnupad et al. |
| 2003/0157330 A1 | 8/2003 | Ostafin et al. |
| 2003/0170196 A1 | 9/2003 | Orsoni et al. |
| 2004/0101566 A1 * | 5/2004 | Cooper et al. ............ 424/489 |
| 2004/0157766 A1 | 8/2004 | Embil et al. |
| 2005/0037087 A1 | 2/2005 | Lapidot et al. |
| 2005/0208134 A1 | 9/2005 | Magdassi et al. |
| 2005/0276807 A1 | 12/2005 | Skurkovich et al. |
| 2006/0128808 A1 | 6/2006 | Arsonnaud et al. |
| 2006/0204530 A1 | 9/2006 | Ramirez et al. |
| 2006/0251687 A1 | 11/2006 | Lapidot et al. |
| 2006/0292093 A1 | 12/2006 | Carola et al. |
| 2007/0003585 A1 | 1/2007 | Clark et al. |
| 2007/0292676 A1 | 12/2007 | Naigertsik et al. |
| 2008/0292560 A1 | 11/2008 | Tamarkin et al. |
| 2009/0081262 A1 | 3/2009 | Toledano et al. |
| 2010/0047357 A1 | 2/2010 | Toledano et al. |
| 2010/0143285 A1 | 6/2010 | Mallard et al. |
| 2011/0052515 A1 | 3/2011 | Kaoukhov et al. |
| 2011/0177951 A1 | 7/2011 | Toledano et al. |
| 2011/0237555 A1 | 9/2011 | Sanchez et al. |
| 2012/0015014 A1 | 1/2012 | Lapidot et al. |
| 2012/0064135 A1 | 3/2012 | Levin et al. |
| 2012/0269874 A1 | 10/2012 | Toledano et al. |
| 2013/0095185 A1 | 4/2013 | Toledano et al. |

FOREIGN PATENT DOCUMENTS

| | | | |
|---|---|---|---|
| CN | 101605537 A | 12/2009 | |
| DE | 44 16 003 A1 | 11/1995 | |
| DE | 19811900 A1 | 9/1999 | |
| DE | 202011100767 U1 | 12/2011 | |
| EP | 0281034 A2 | 9/1988 | |
| EP | 0 462 388 A2 | 12/1991 | |
| EP | 0 478 326 A1 | 4/1992 | |
| EP | 0 581 651 A2 | 2/1994 | |
| EP | 0 680 753 A1 | 11/1995 | |
| EP | 0 934 773 A2 | 8/1999 | |
| EP | 0 941 761 A2 | 9/1999 | |
| EP | 0 972 563 A1 | 1/2000 | |
| EP | 0972563 A1 * | 1/2000 | ............ B01J 13/22 |
| EP | 1116516 A1 | 7/2001 | |
| EP | 1511802 B1 | 9/2010 | |
| FR | 2703927 A1 | 10/1994 | |
| FR | 2774906 A1 | 8/1999 | |
| FR | 2780901 A1 | 1/2000 | |
| GB | 1399344 A | 7/1975 | |
| GB | 2 416 524 A | 2/2006 | |
| JP | 01-113436 A | 5/1989 | |
| JP | 02-002867 A | 1/1990 | |
| JP | 02-040302 A | 2/1990 | |
| JP | 02-251240 A | 10/1990 | |

(56) References Cited

FOREIGN PATENT DOCUMENTS

| | | |
|---|---|---|
| JP | 03-229634 A | 10/1991 |
| JP | 03-243663 A | 10/1991 |
| JP | 07173452 A | 7/1995 |
| JP | 09110463 A | 4/1997 |
| JP | 09-235217 A | 9/1997 |
| JP | 02-292824 A | 10/2002 |
| JP | 03-534249 A | 11/2003 |
| JP | 05-043208 A | 2/2005 |
| JP | 05-513146 A | 5/2005 |
| JP | 05-528152 A | 9/2005 |
| JP | 05-529636 A | 10/2005 |
| RU | 98105780 A | 12/1999 |
| RU | 2314093 C2 | 1/2008 |
| WO | 94/04260 A1 | 3/1994 |
| WO | 94/04261 A1 | 3/1994 |
| WO | 97/07676 A1 | 3/1997 |
| WO | 97/32561 A1 | 9/1997 |
| WO | 97/40106 A1 | 10/1997 |
| WO | 97/45367 A1 | 12/1997 |
| WO | 98/15183 A1 | 4/1998 |
| WO | 98/31333 A1 | 7/1998 |
| WO | 99/03450 A1 | 1/1999 |
| WO | 00/09652 A2 | 2/2000 |
| WO | 00/25761 A1 | 5/2000 |
| WO | 0025908 A1 | 5/2000 |
| WO | 0047236 A1 | 8/2000 |
| WO | 00/71084 A1 | 11/2000 |
| WO | 00/72806 A2 | 12/2000 |
| WO | 01/12221 A1 | 2/2001 |
| WO | 0113924 A2 | 3/2001 |
| WO | 01/58451 A1 | 8/2001 |
| WO | 01/80823 A2 | 11/2001 |
| WO | 02/085113 A1 | 10/2002 |
| WO | 03/003497 A1 | 1/2003 |
| WO | 03/034973 A1 | 5/2003 |
| WO | 03/039510 A1 | 5/2003 |
| WO | 03/066209 A1 | 8/2003 |
| WO | 03/086419 A1 | 10/2003 |
| WO | 03/104319 A1 | 12/2003 |
| WO | 2004/064769 A2 | 8/2004 |
| WO | 2004/064803 A1 | 8/2004 |
| WO | 2004/069135 A2 | 8/2004 |
| WO | 2004/069216 A1 | 8/2004 |
| WO | 2004/081222 A2 | 9/2004 |
| WO | 2005/009604 A1 | 2/2005 |
| WO | 2007/000316 A1 | 1/2007 |
| WO | 2007/015243 A2 | 2/2007 |
| WO | 2007/036939 A2 | 4/2007 |
| WO | 2008/002637 A2 | 1/2008 |
| WO | 2008/057411 A1 | 5/2008 |
| WO | 2008/093346 A2 | 8/2008 |
| WO | 2008/093347 A2 | 8/2008 |
| WO | 2009/148584 A1 | 12/2009 |
| WO | 2011/049547 A1 | 4/2011 |
| WO | 2012037000 A1 | 3/2012 |

OTHER PUBLICATIONS

C.-C. Chung et al., "Aqueous Synthesis of Y2O2S:Eu/Silica Core-Shell Particles", J. Am. Ceram. Soc. 88 (5) 1341-1344 (2005).
H. Dun et al., "Layer-by-Layer Self-Assembly of Multilayer Zirconia Nanoparticles on Silica Spheres for HPLC Packings", Anal. Chem. 2004, 76, 5016-5023.
S. R. Hall et al., "Cocondensation of Organosilica Hybrid Shells on Nanoparticle Templates: A Direct Synthetic Route to Functionalized Core-Shell Colloids", Langmuir 2000, 16, 1454-1456.
I. Haq et al., "Preparation and properties of uniform coated inorganic colloidal particles 9. Titania on copper compounds", Colloids and Surfaces A: Physicochemical and Engineering Aspects, 81 (1993) 153-159.
L. L. Hench et al., "The Sol-Gel Process", Chem. Rev. 1990, 90, 33-72.
W. P. Hsu et al., "Paper Whiteners, 1. Titania Coated Silica", Journal of Colloid and Interface Science, 156, 56-65 (1993).
R. K. Iler, "The Chemistry of Silica", Wiley-Interscience publication, 1979, 510-533.
F. Iskandar et al., "Control of the morphology of nanostructured particles prepared by the spray drying of a nanoparticle sol", Journal of Colloid and Interface Science 265 (2003) 296-303.
F. Iskandar et al., "Preparation of microencapsulated powders by an aerosol spray method and their optical properties", Advanced Powder Technology vol. 14, No. 3, pp. 349-367 (2003).
J.-H. Jean et al., "Y2O2S:Eu Red Phosphor Powders Coated with Silica", J. Am. Ceram. Soc. 83 (8) 1928-34 (2000).
N. Lapidot et al., "Advanced Sunscreens: UV Absorbers Encapsulated in Sol-Gel Glass Microcapsules", Journal of Sol-Gel Science and Technology, 26, 67-72, 2003.
O. V. Makarova et al., "Adsorption and Encapsulation of Fluorescent Probes in Nanoparticles", J. Phys. Chen. B. 1999, 103, 9080-9084.
Matijevi et al., "Coating of Nanosize Silver Particles with Silica", Journal of Colloid and Interface Science 221, 133-136 (2000).
J. Merikhi et al., "Adhesion of Colloidal SiO2 Particles on ZnS-Type Phosphor Surfaces", Journal of Colloid and Interface Science 228, 121-126 (2000).
Mikrajuddin et al., "Stable photoluminescence of zinc oxide quantum dots in silica nanoparticles matrix prepared by the combined sol-gel and spray drying method", Journal of Applied Physics, vol. 89, No. 11, pp. 6431-6434.
T. Nakasuka, "Surface Modification of Inorganic Pigments with Organic UV Absorbers", Colloids and Surfaces, 34 (1988/89) 323-334.
C. Rottman et al., "Advanced Sunscreens: UV Absorbers Entrapped in Sol-Gel Glass Microcapsules", Journal of Sol-Gel Science and Technology, vol. 23, pp. 268-270, 2002.
C. Rottman et al., "Advanced Sunscreens: UV Absorbers Entrapped in Glass Microcapsules", Euro Cosmetics Jan. 2000, pp. 20-22.
H. Tatapudy et al., "Benzoyl Peroxide Microcapsules 1. Preparation of Core Material", Indian Drugs, 32(6):239-248, 1995.
M. P. B. van Bruggen, "Preparation and Properties of Colloidal Core-Shell Rods with Adjustable Aspect Ratios", Langmuir 1984, 14, 2245-2255.
G. R. Villalobos et al., "Protective Silica Coatings on Zinc-Sulfide-Based Phosphor Particles", J. Am. Ceram. Soc. 85 (8) 2128-30 (2002).
H. Wang et al., "Effect of Polyelectrolyte Dispersants on the Preparation of Silica-Coated Zinc Oxide Particles in Aqueous Media", J. Am. Ceram. Soc. 85 (8) 1937-40 (2002).
P. Wilhelm et al., "On-line tracking of the coating of nanoscaled silica with titania nanoparticles via zeta-potential measurements", Journal of Colloidal and Interface Science, 293 (2006) 88-92.
J. Yuan et al., "Organic Pigment Particles Coated with Colloidal Nano-Silica Particles via Layer-by-Layer Assembly", Chem. Mater. 2005, 17, 3587-3594.
Federal Register vol. 67, No. 94 and 40 CFR Part 180, May 15, 2002 / Rules and Regulations.
"Martindale: The extra Pharmacopeia," Pharmaceutical Press, pp. 1093-1095, 1999.
Bashir and Maibach, The Chemistry and Manufacture of Cosmetics V1 Chapter 5 third ed. pp. 163-182 (2000).
Beelen et al., "The Role of Aging on the Formation of Porous Silica," Preparation of Catalysts VI, pp. 33-48, Elsevier Science B.V. (1995).
Breneman et al. "Double-blind, randomized, vehicle-controlled clinical trial of once-daily benzoyl peroxide/clindamycin topical gel in the treatment of patients with moderate to severe rosacea" (Int. J. Derma. 43, 381-387 (2004).
Bugosh, "Colloidal Alumina—The Chemistry and Morphology of Colloidal Boehmite", Chemistry and Morphology of Colloidal Boehmite, 65:1789-1793 (1961).
Fireman et al., "A Look at emerging delivery systems for topical drug products" Derma. Ther. 24:477-488 (2011).
International Search Report dated Apr. 16, 1999, for PCT/IL2008/000140 (WO2008/093346 A3).
James J. Leyden, Comparison of the Efficacy and Safety of a Combination Topical Gel Formulation of Benzoyl Peroxide and

(56) References Cited

OTHER PUBLICATIONS

Clindamycin with Benzoyl Peroxide, Clindamycin and Vehicle Gel in the Treatments of Acne Vulgaris, Am J Clin Dermatol 2(1): 33-39 (2001).

Kim et al., "Monodisperse hollow titania nanospheres prepared using a cationic colloidal template", Journal of Colloid and Interface Science, 304(2):370-377 (2006).

Kortesuo et al., "Effect of synthesis parameters of the sol-gel-processed spray-dried silica gel microparticles on the release rate of dexmedetomidine", Biomaterials, 23:2795-2801 (2002).

Kortesuo et al., "In vitro evaluation of sol-gel processed spray dried silica gel microspheres as carrier in controlled drug delivery", International Journal of Pharmaceutics, 200:223-229 (2000).

Liz-Marzan et al., "Synthesis of Nanosized Gold-Silica Core-Shell Particles," Langmuir, 12:4329-4335 (1996).

Maibach., "Reduction of Skin Irritancy with Microsponge® Topical Delivery" Aesthetic Dermatology, Touch Briefings, pp. 45-47 (2008).

Montes et al., "Topical Treatment of Acne Rosacea with Benzoyl Peroxide Acetone Gel" Cutis 32:185-190 (1983).

Nokhodchi, Iranian J. of Pharmaceutical Sciences, Summer 2005: 1(3): 131-142 (2005).

Stober process from Wikipedia, http://en.wikipedia.org/wiki/St%C3%B6ber_process, downloaded May 8, 2013.

Takeuchi et al., "Solid dispersion particles of tolbutamide prepared with fine silica particles by the spray-drying method", Powder Technology, 141:187-195 (2004).

Wenninger et al., "International Cosmetic Ingredient Dictionary and Handbook", 2:1140-1147 (2000).

Wester et al., "Controlled release of benzoyl peroxide from a porous microsphere polymeric system can reduce topical irritancy" J. Am. Acad. Derma. 24:720-726 (1991).

www.lotioncrafter.com, http://www.lotioncrafter.com/dimethyl-isosorbide-dnti.html downloaded [May 3, 2013].

Yamasaki et al., "Increased serine protease activity and cathelicidin promotes skin inflammation in rosacea" Nature Medicine (13)(8):975-980 (Aug. 2007).

Brinker et al. "Sol-Gel Science, The Physics and Chemistry of Sol-Gel Processing" Academic Press, Inc., San Diego, CA, pp. 104-105, 134-137, 146-147, and 150-151. (1990).

Brinker et al. "Sol-Gel Science, The Physics and Chemistry of Sol-Gel Processing" Academic Press, Inc., Chapter 3, pp. 104, 105, 134, 135, 146, 147, 150 and 151. (1990).

"Ludox TM-50 colloidal silica", Sigma-Aldrich, website: http://www.sigmaaldrich.com/catalog/product/aldrich/420778?lang=en&region=US, downloaded Aug. 29, 2012.

Ralph K. Iler "The Chemistry of Silica, Solubility, Polymerization, Colloid and Surface Properties, and Biochemistry" John Wiley & Sons, pp. 366-367 (1979).

Verginis, "Cutis Benzoyl Peroxide Rosacea Study Summary" downloaded from (http://www.rosacea-treatment-clinic.com.au/Benzoyl-Peroxide/Benzoyl-Peroxide-Acetone.html) (May 2010).

Wenninger et al., "International Cosmetic Ingredient Dictionary and Handbook" Seventh Edition, vol. 2, pp. 1656-1662 (1997).

Luo, Mingsheng and Tianhui Gao "The Extra Pharmaceutical Necessities", Sichuan Science and Technology Press, pp. 23-28, published on Mar. 31, 1993 (with English translation of relevant parts).

Tjandra et al.,"Interaction between Silicates and Ionic Surfactants in Dilute Solution" Langmuir, 22:1493-1499 (2006).

\* cited by examiner

METAL OXIDE COATING OF WATER INSOLUBLE INGREDIENTS

FIELD OF THE INVENTION

The present invention generally relates to particles comprising metal oxide coating layer, compositions comprising the particles and to a method for their preparation.

BACKGROUND OF THE INVENTION

Metal oxides have been used as encapsulating materials and as matrices for various applications such as cosmetics, biomaterials, optics, laser, florescence, etc. using a variety of methods.

Shells consisting of hybrid inorganic-organic structures with bulk and surface properties that are compositionally controlled have been described in Hall, Simon, R., et al, Cocondensation of Organosilica Hybrid Shells on Nanoparticle, Templates: A Direct Synthetic Route to Functionalized Core—Shell Colloids, *Langmuir*, 16:1454-1456, 2000.

The formation of silica shells on core silver particles by a modified Stöber process is reported by Matijevi et al in *Journal of Colloid and Interface Science*, Volume 221, Issue 1, 1 Jan. 2000, Pages 133-136. They also report on the formation of spherical particles of Cu(II) basic carbonate coated with amorphous titania by hydrolysis of Ti(IV) butoxide in *Colloids and Surfaces A: Physicochemical and Engineering Aspects*, Volume 81, 13 Dec. 1993, Pages 153-159. In this report they show how the thickness of the shell could be varied by altering the experimental conditions. White pigments (whiteners) were prepared by coating monodispersed silica particles with titania. The hiding power of this powder was evaluated as a function of the particle diameter, the thickness of the titania shell, and the calcination temperature. Matijevi et al, *Journal of Colloid and Interface Science*, Volume 156, Issue 1, 1 Mar. 1993, Pages 56-65.

Colloidal boehmite (AlOOH) rods were used as cores for the preparation of rods with a silica shell as described in van Bruggen, M. P. B., Preparation and Properties of Colloidal Core—Shell Rods with Adjustable Aspect Ratios, *Langmuir*, 14:2245-2255, 1998.

A method for the encapsulation of fluorescent molecule into silica "nanobubbles" has been reported in Makarova, Olga V., et al., Adsorption and Encapsulation of Fluorescent Probes in Nanoparticles, *J. Phys. Chem. B*, 103:9080-9084, 1999. Bugnon, Philippe, (Bugnon, Philippe, Surface treatment of pigments. Treatment with inorganic materials, *Progress in Organic Coatings* 29: 39-43, 1996) has reported novel treatments of pigments with inorganic materials. Mikrajuddin, et al., (Mikrajuddin, et al, Stable photoluminescence of zinc oxide quantum dots in silica nanoparticles matrix prepared by the combined sol-gel and spray drying method, *Journal of Applied Physics*, 89:11, 2001) reported a ZnO/SiO2 nanocomposite with improved photoluminescence stability over ZnO colloids.

A spray drying approach has been used to apply 15-nm-thick $SiO_2$ continuous coatings onto ZnS:Ag phosphor particles as described in Villalobos, Guillermo, R., et al., Protective Silica Coatings on Zinc-Sulfide-Based Phosphor Particles, *J. Am. Ceram. Soc.*, 85(8):2128-2130, 2002.

Iskandar et al. have reported the preparation of microencapsulated powders by an aerosol spray method. The powders prepared by mixing two type of sols or sol-aqueous mixture precursor solution (Iskandar, Ferry, et al, Preparation of microencapsulated powders by an aerosol spray method and their optical properties, *Advanced Powder Technol.* 14(3):349-367, 2003). Iskandar et al. (Control of the morphology of nanostructured particles prepared by the spray drying of a nanoparticle sol. J Colloid Interface Sci., 265(2):296-303, 2003) additionally described the parameters influencing particles morphology by spray drying of silica nanoparticle sol.

Silica coating using layer by layer technique has been described in Dun, Huijuan, et al, Layer-by-Layer Self-Assembly of Multilayer Zirconia Nanoparticles on Silica Spheres for HPLC Packings, *Anal, Chem.*, 76:5016-5023, 2004; Yuan, Junjie, et al., Organic Pigment Particles Coated with Colloidal Nano-Silica Particles via Layer-by-Layer Assembly, *Chem. Mater.*, 17(4):3587-3594, 2005; Chung, Chau-Chyun, et al., Aqueous Synthesis of $Y_2O_2S$:Eu/Silica Core-Shell Particles, *J. Am. Ceram. Soc.*, 88(5):1341-1344, 2005.

Y2O2:Eu red phosphor Powders coated with silica using sol-gel and heterocoagulation techniques were described in Jean, Jau-Ho, et al., $Y_2O_2S$:Eu Red Phosphor Powders Coated with Silica, *J. Am. Ceram. Soc.*, 83(8):1928-1934, 2000.

Wilhelm, P., et al., (Wilhelm, P., et al, On-line tracking of the coating of nanoscaled silica with titania nanoparticles via zeta-potential measurements, Journal of Colloid and Interface Science, 293:88-92, 2006) reported nanoscaled spherical particles which were directly coated with titania nanoparticles by means of heterogenic coagulation.

The interaction between colloidal silica particles and the surface of ZnS-type phosphors has been studied in Merikhi, J., et al., Adhesion of Colloidal $SiO_2$ Particles on ZnS-Type Phosphor Surfaces, *Journal of Colloid and Interface Science*, 228:121-126, 2000.

Sodium Silicate utilized to obtain a $SiO_2$ coating on particles has been described in Wang, Hongzhi, et al., Effect of Polyelectrolyte Dispersants on the Preparation of Silica-Coated Zinc Oxide Particles in Aqueous Media, *J. Am. Ceram. Soc.*, 85(8):1937-1940, 2002; U.S. Pat. No. 2,885,366; U.S. Pat. No. 3,826,670.

The sources of silica gels and factors controlling gel characteristics were described in Iler Ralph K., The Chemistry of Silica, Wiley-Interscience publication, 1979, pp. 510-533. U.S. Pat. No. 6,303,290 describes the encapsulation of biomaterials in porous glass-like matrices prepared via an aqueous colloidal sol-gel process. This process includes entrapment of the biomaterial in silica cages forms by controlling the gel characteristics.

JP02-002867 and JP 02-251240 disclose spherical particles made principally of silica, prepared by coprecipitation on of silica and UV filters such as benzophenone derivatives or dibenzoylmethane derivative, prepared in a water-in-oil emulsion.

U.S. Pat. No. 6,875,264 discloses a multilayer effect pigment including a transparent substrate, a layer of high refractive index material on the substrate, and alternating layers of low refractive index and high refractive index materials on the first layer. The high refractive index material may be titanium dioxide and the low refractive index material may be silicon dioxide.

U.S. Pat. No. 6,090,399 discloses a controlled release composition comprising one or more biologically active compounds incorporated into a metal oxide glass having a porous matrix.

U.S. Pat. No. 7,001,592 and U.S. Pat. No. 7,037,513 disclose a composition for topical application, e.g., a bodywash, where the additive contains a sol-gel encapsulated active either a sunscreen or a non-sunscreen. U.S. Pat. No.

7,052,913 discloses a biocompatible matrices, such as sol-gels encapsulating a reaction center, which may be administered to a subject for conversion of prodrugs into biologically active agents.

U.S. Pat. Nos. 6,303,149, 6,238,650, 6,468,509, 6,436,375, US2005037087, US2002064541, and International publication Nos. WO 00/09652, WO00/72806, WO 01/80823, WO 03/03497, WO 03/039510, WO00/71084, WO05/009604, and WO04/81222, disclose sol-gel microcapsules and methods for their preparation. EP 0 934 773 and U.S. Pat. No. 6,337,089 teach microcapsules containing core material and a capsule wall made of organopolysiloxane, and their production. EP 0 941 761 and U.S. Pat. No. 6,251,313 also teach the preparation of microcapsules having shell walls of organopolysiloxane. U.S. Pat. No. 4,931,362 describes a method of forming microcapsules or micromatrix bodies having an interior water-immiscible liquid phase containing an active, water-immiscible ingredient.

Another media, which can be utilized to protect sensitive ingredients, is doping within sol-gel matrices. In this method, monoliths, particles or other forms (such as thin films) are prepared, and the active ingredient is immobilized in the pores of the sol-gel matrix. The sol-gel matrix is doped with small amounts of the active ingredient. This method was utilized in WO98/31333, U.S. Pat. No. 6,495,352, and U.S. Pat. No. 5,292,801.

None of the prior art references teach or disclose a method for coating a solid, water insoluble particulate matter by a metal oxide layer with the ability to form and grow a coarse and dense layer on the surface of said particulate matter.

Thus there is a widely recognized need and will be highly advantageous to have a new process for metal oxide coating of a water insoluble particulate matter, enabling the growth of a metal oxide layer on said water insoluble particulate matter to the desired thickness. There is additionally a need for compositions especially for dermatological or agricultural use, characterized by the ability to isolate the active agent from the surrounding (by reducing its leaching through the metal oxide coating layer) thus lowering the side effects and toxicity associate with the active agent, and yet which are efficient at controlling the release of the active agent to the loci to be treated.

SUMMARY OF THE INVENTION

The present invention is based on the finding of a manner of obtaining a thick and dense coating of metal oxide on a solid water-insoluble particulate matter. The formation of the metal oxide layer by the new method is irreversible, i.e. it does not erode or disintegrate upon dispersion in water. The new method comprises treating the solid water-insoluble particulate matter with a first cationic additive in an aqueous medium to obtain positive zeta potential of the particulate matter; coating the particulate matter by precipitation of a metal oxide salt; and aging the coating layer. The coating and aging steps may be repeated one to several times, preferably two to three times, most preferably two more times. The process may include additional steps as will be detailed below such as treating the so formed coating with a cationic additive to obtain a positive zeta potential of the coating, in order to modify the surface charge of the metal oxide layer to make it reactive for further coating by an additional metal oxide layer in a similar manner to that described above; a step of separating the coated particulate matter; and optionally a step of washing and redispersing the obtained coated particulate matter in an aqueous medium.

The new method of preparation enables the formation and growth of a thick layer or layers of a metal oxide coating on the particulate matter. This is particularly advantageous for certain uses where the active ingredient should be isolated, from its surroundings with an ability to be gradually released through the metal oxide layer. Exemplary uses are dermatological or cosmetic uses as well as in the case of pesticides for home, horticultural or agricultural use.

The present invention is further based on the finding that it is possible to coat a water insoluble particulate matter such as pharmaceutically, cosmetic or agrochemical agents with a metal oxide layer to provide a barrier to the release of the active agent therefrom, thus delivering the active agent to the surface to be treated in a controlled manner. Preferred is coating intended to achieve substantially the same or a larger therapeutic effect of the active agent and reduced side effects compared to an uncoated composition of the active agent.

According to one aspect of the present invention there is provided a process for coating a solid, water-insoluble particulate matter, with a metal oxide comprising:

(a) contacting the solid, water-insoluble particulate matter, with a cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon; and (c) aging said coating layer.

According to another aspect of the present invention there is provided coated particulate matter obtained by the process as described in the present invention.

According to yet another aspect of the present invention there is provided a pharmaceutical, cosmetic or cosmeceutical composition for topical administration comprising a carrier; and a plurality of particles, each of said particles comprising a solid, water insoluble dermatologically active agent, coated by a metal oxide layer.

According to still another aspect of the present invention there is provided a composition for topical administration comprising:

a plurality of particles, each of said particles comprising a solid, water insoluble dermatologically active agent, coated by a metal oxide layer; and a carrier;

said composition having reduced side effects and at least essentially the same therapeutic effect as compared to a reference composition; the difference between said composition and the reference composition being in that in the latter the active agent is not coated.

According to an additional aspect of the present invention there is provided a method for treating a surface condition in a subject, comprising topically administering onto the surface a pharmaceutical, cosmetic or cosmeceutical composition as described in the present invention.

According to yet additional aspect of the present invention there is provided a method for treating a surface condition in a subject, comprising topically administering onto the surface a composition comprising coated particulate matter prepared by the process described in the present invention.

According to still additional aspect of the present invention there is provided use of coated particulate matter, the particulate matter being a solid, water insoluble topically dermatologically active agent, coated by a metal oxide layer, for the preparation of a medicament for topical administration on the skin or mucosal membrane.

According to still additional aspect of the present invention there is provided use of coated particulate matter according to the process of the present invention, the particulate matter being a topically dermatologically active agent, for the preparation of a medicament for topical administration on the skin or mucosal membrane.

According to a further aspect of the present invention there is provided compositions for pest control comprising a pesticide, said pesticide being a solid, water-insoluble particulate matter, coated by a metal oxide layer.

According to a yet further aspect of the present invention there is provided compositions for pest control comprising coated particulate matter obtained by the process described in the present invention, said particulate matter being a pesticide.

DETAILED DESCRIPTION OF THE INVENTION

Figure 1A:
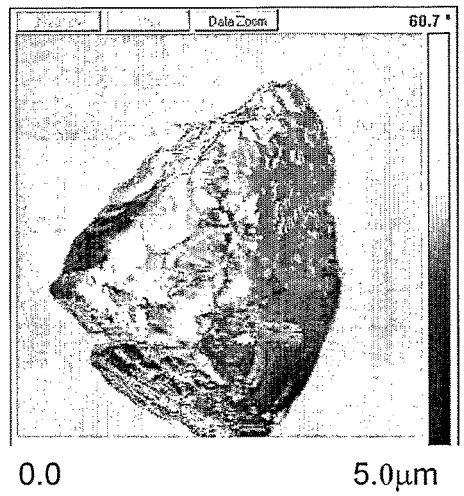
FIG. 1 is an Atomic Force Microscope picture of Benzoyl Peroxide, before (a) and after (b) coating with silica, according to Example 1.
Figure 1B:
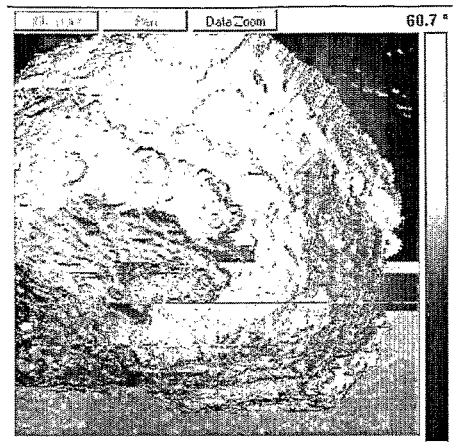
Figure 2A:
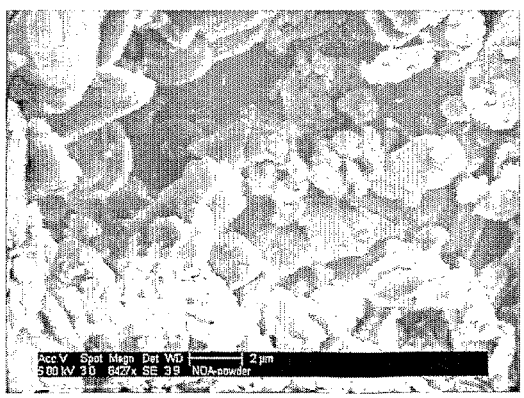
FIG. 2 is a High Resolution Scanning Electron Microscope picture of Bifenthrin before (a&c) and after (b&d) coating with silica, according to example 5.
Figure 2B:
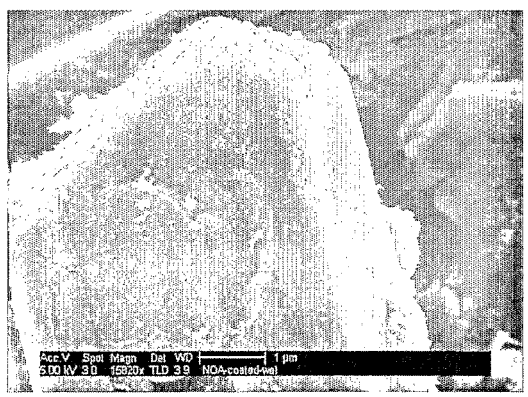
Figures 2C, 2D:
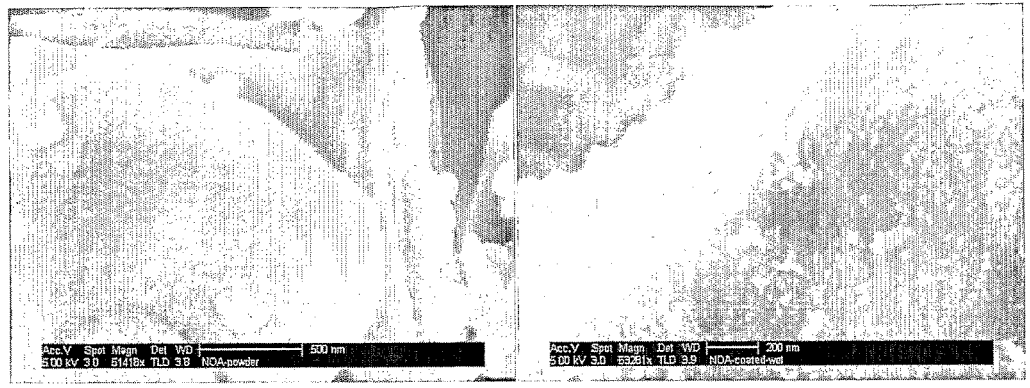
Figure 3A:
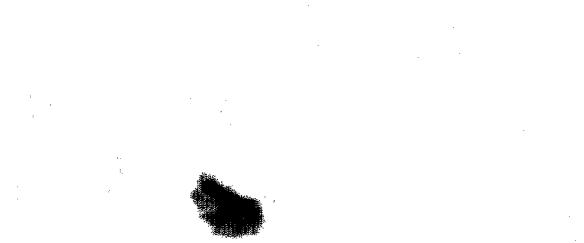
FIG. 3 is a Transmition Electron Microscope picture of Bromo-Benzyl, before (a) and after (b) coating with silica, according to example 4.
Figure 3B:
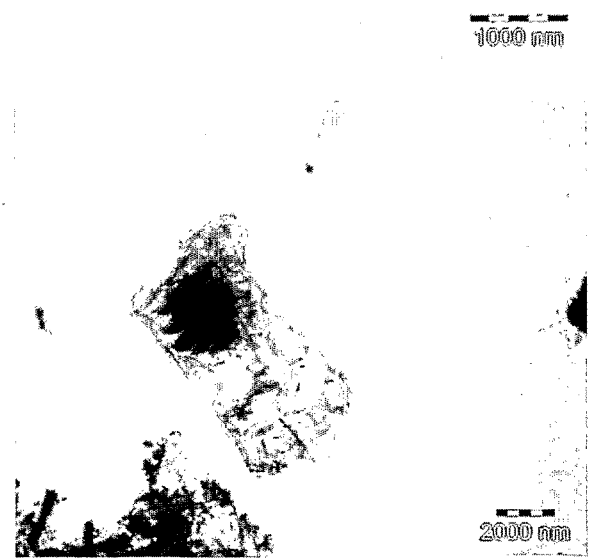

The present invention relates to a process for coating a solid, water-insoluble particulate matter, with a metal oxide comprising:

(a) contacting the solid, water-insoluble particulate matter, with a cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon; and (c) aging said coating layer.

As used herein the term "solid, water-insoluble particulate matter" refers to a solid material having solubility in water of less than 1% w/w, typically less than 0.5% and at times less than 0.1% w/w at room temperature (20° C.).

The "solid, water-insoluble particulate matter" constitutes the "core" of the particles obtained by the process. The solid, water-insoluble particulate matter, is preferably in such a state of subdivision that it can be suspended in water, e.g. in the form of a finely-divided powder having a $D_{90}$ (see definition below), preferably in the range of 0.3-50 micron. Such a particulate matter can readily be suspended in an aqueous systems by stirring, with or without the aid of a surfactant.

In the present invention the terms "solid, water-insoluble particulate matter" and "particulate matter" will be used interchangeably.

Step (a) of the process may further comprise reducing the particle size of the particulate matter to the desired particle size for example by milling.

The core (i.e. solid, water insoluble particulate matter) may be of any shape for example rod-like, plate-like, ellipsoidal, cubic, or spherical shape.

The size of the particles as will be referred to herein refers to $D_{90}$ meaning that 90% of the particles have the stated dimension or less (measured by volume). Thus, for examples, for spherical particles stated to have a diameter of 10 micrometer ("microns"), this means that the particles have a $D_{90}$ of 10 microns. The $D_{90}$ may be measured by laser diffraction. For particles having a shape other than spheres, the $D_{90}$ refers to the mean average of the diameter of a plurality of particles.

In the case of cores having a spherical shape, the mean diameter may be in the range of 0.3 to 90 microns, preferably 0.3 to 50 microns, more preferably 1 to 50, even more preferably 5 to 30 microns.

For generally cubic-shaped cores or cores having a shape resembling that of a cube, the mean size of a side may be in the range 0.3 to 80 microns, preferably 0.3 to 40 microns, more preferably 0.8 to 40, even more preferably 4 to 15 microns.

For rod-like shaped, ellipsoidal-shaped and plate-like shaped cores, the largest dimension (that of the longest axis) is typically in the range 10 to 100 microns, preferably 15 to 50 microns; and the smallest dimension is typically in the range 0.5 to 20 microns and more preferably 2 to 10 microns.

As used herein, unless otherwise indicated, the term "particle" refers to the metal oxide coated particulate matter.

It is appreciated that some of the particles obtained by the process may at times be formed from two or more original particles of the solid, water-insoluble particulate matter and may accordingly include at times more than one core, such cores being separated from each other by a metal oxide region.

The core may be an organic or inorganic material. Preferably the core is composed of a material other than a metal oxide.

The weight of the solid, water-insoluble particulate matter (core material) based on the total weight of the particle may be in the range 97%-50% w/w. The core material may be in a crystalline form, amorphous form, or combination thereof. The core material may be a cosmetically, pharmaceutically or an agrochemical active ingredient.

Preferably the process comprising subjecting the coated particulate matter to one or more steps of precipitation of metal oxide salt, followed by aging treatment.

In order to obtain a more robust coating, the particles obtained by the above process (following step (c)) may be subject to further, optional, processing steps to cause precipitation of more metal oxide on the initially formed metal oxide layer. Such further processing may include also an aging step, similar to step (c). Additionally, the precipitation step of the additional processing may also involve a step, similar to step (a) above, in which a positive zeta potential is formed on the coating layer (i.e. the metal oxide coating layer), through the addition of a cationic additive, which may be the same or may be different to those used in said step (a). The further processing step may be repeated one, two, three or a plurality of more times.

According to a preferred embodiment of the present invention step (c) further comprising after aging, separating the coated particulate matter from the dispersing aqueous medium and optionally rinsing and redispersing the obtained coated particulate matter in an aqueous medium.

Moreover according to a preferred embodiment of the present invention, step (c) further comprises after redispersing the coated particulate matter in an aqueous medium, adding a second cationic additive to obtain a positive zeta potential of the coating layer.

Alternatively, the further processing steps may be conducted without the addition of a cationic additive. In such a case, the process preferably comprises:

(a) contacting the solid, water-insoluble particulate matter, with a first cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon;

(c) aging said coating layer to obtain first coated particulate matter;

(d) coating the first coated particulate matter by precipitation of a metal oxide salt onto the surface of the particulate matter, forming a metal oxide layer thereon; and (e) aging said coating layer to obtain second coated particulate matter;

The process may further comprise:

(f) coating the second coated particulate matter by precipitation of a metal oxide salt onto the surface of the particulate matter, forming a metal oxide layer thereon; and (g) aging said coating layer to obtain third coated particulate matter.

In the absence of a cationic additive in the further processing steps the positive zeta potential in step (a) is preferably less than +150 mV, and more preferably in the range +60 mV to +130 mV. The zeta potential of the coated particulate matter after aging may be in the range 0 mV to −60 mV.

In order to ensure the deposition of further metal oxide layers in the further processing steps by electrostatic interaction and also to control the thickness of the metal oxide (e.g. silica) layers it is preferable to use a second cationic additive.

According to a preferred embodiment of the present invention the process comprises:

(a) contacting the solid, water-insoluble particulate matter, with a first cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon;

(c) aging said coating layer to obtain first coated particulate matter;

(d) contacting the first coated particulate matter with a second cationic additive in an aqueous medium to obtain a dispersion of said first coated particulate matter having a positive zeta potential and further processing the dispersion through steps (b) and (c) to obtain a further processed, coated particulate matter.

The process may further comprise, processing the coated particulate matter obtained in (d) through another step (d).

Preferably the coated particulate matter and the second cationic additive are mixed, and most preferable said mixing is under vigorous stirring (e.g. mixer speed above 1000 rpm).

The first cationic additive used in step (a) of the process has a dual effect: to increase the zeta potential of the particulate matter as will be described below, and also to serve as a wetting agent, thus allowing dispersion of the particulate matter as discrete core particles, where each core particle is individually suspended in the aqueous medium.

It is important that the surface of the particulate matter be reactive or be made subject to bonding with metal oxide layer.

The purpose of step (a) is to modify the zeta potential of the particulate matter by using a cationic additive such that it will be made reactive to the attachment of the metal oxide layer.

For preparing the core material of the particles, the particulate matter ought to be suitably coated with a first cationic additive, such that it can be attached to the precipitated metal oxide salt. The particulate matter is contacted with a first cationic additive, for example by mixing it with a solution of a cationic surfactant or cationic polymer. Cationic surfactants are particularly effective in being adsorbed upon the surface of the particulate matter and they need to be used in sufficient amount to provide a positive zeta potential of the particulate matter (preferably in the range above 0 mV and up to +150 mV, more preferably +60 mV to +130 mV).

A monolayer of the cationic additive is preferred, but the coating need not be continues. It is sufficient that there are at least spots of cationic additive. These spots will then serve as anchors for the attachment of the metal oxide layer. It is preferred that there are fairly uniform distribution of these anchoring points on the core surface so that as the metal oxide layer builds up it will bridge over and be firmly attached to the core.

Preferably the process comprising repeating step (d) one or two additional times, most preferably one additional time.

According to one preferred embodiment said first and said second cationic additive are the same.

According to another preferred embodiment said first and said second cationic additive are different.

Most preferably the first cationic additive is a surfactant and the second cationic additive is a cationic polymer.

According to a preferred embodiment of the present invention step (c) further comprising after aging, separating the coated particulate matter from the dispersing aqueous medium and optionally rinsing and redispersing the obtained coated active ingredient in an aqueous medium.

Preferably the separation of the coated particulate matter is conducted by a method such as filtration centrifugation, dialysis, or by evaporation of the aqueous medium.

Further according to a preferred embodiment of the present invention, step (b) comprises contacting said dispersion obtained in (a) with a metal oxide salt under conditions so as to precipitate the metal oxide salt onto surface of the particulate matter, yielding a coating layer thereon.

Additionally according to a preferred embodiment of the present invention, step (b) comprises adding a metal oxide salt to yield a value of pH 7-11; and acidifying to yield a pH value of 1-3 (more preferably a pH of about 2).

More preferably step (b) comprises adding a metal oxide salt to reach a value of 8-10; and acidifying to obtain a value of 0.1-3 (more preferably a pH of about 2).

When the particulate matter is an acidic compound it may be preferred to add a metal oxide salt to reach a pH value of 7-8; and acidifying to obtain a value of 1-3.

Preferably step (b) further comprising adjusting the pH of the dispersion obtained in (a) to a value in the range 5.5-8 before adding a metal oxide salt, more preferably to a pH value in the range 7-8 before adding a metal oxide salt.

The purpose of the pH adjustment of the dispersion to a value between 5.5-8 is to form negatively charged metal oxide species that will be bound to the positively charged particulate matter surface thus enabling the attachment of the metal oxide layer on the surface of the particulate matter. Further at this pH range the growth of larger discrete metal oxide particles at the expense of smaller particles is preferred, thus forming a denser layer of metal oxide on the surface of the particulate matter.

According to a preferred embodiment of the present invention step (b) is repeated at least 1-3 additional times (i.e. one, two or three more times). Most preferably step (b) is repeated one additional time.

According to a preferred embodiment of the present invention the positive zeta potential in step (a) is less than +150 mV (+150 or less, i.e. above 0 and up to +150 mV), and more preferably in the range +60 mV to +130 mV).

According to a preferred embodiment of the present invention the positive zeta potential in step (d) is less than +150 mV (+150 or less, i.e. above 0 and up to +150 mV), more preferably in the range +5 mV to +130 mV, and most preferably +10 to +100 mV.

The aging in step (c) is crucial for obtaining a strengthened and dense layer of metal oxide.

According to a preferred embodiment of the present invention step (c) comprises raising the pH to a value in the range 6.5-9.5, preferably to a range of 7.5-8.5, and mixing, e.g. by stirring, the suspension (dispersion) in this pH range for a period of at least 12 h (twelve hours). Preferably stirring is for 12-72 h, more preferably at least 20 h (for example 20-72 h), even more preferably for 36 h-72 h, and most preferably for 40-50 h.

The stirring is preferably a gentle stirring, preferably in the range 200-500 rpm.

An indication for the completion of aging can be obtained by constant zeta potential measurements upon repeated increased dilutions. Further, upon completion of aging, the filtration will be easy to perform (due to the hard metal oxide layer formed) and the obtained cake will be easily redispersed in an aqueous medium to form a dispersion of particles.

Without being bound to theory, it is believed that at the above pH range of 6.5-9.5 (preferably pH 7.5-8.5) there is a preferential growth of the larger metal oxide particles (i.e. the metal oxide nanoparticles in the formed metal oxide layer), which are formed during precipitation of the metal oxide, at the expense of the smaller particles (by the Ostwald-Ripening mechanism).

The purpose of aging in step (c) is to obtain a strengthened and denser layer of metal oxide and therefore to enable the growth of the metal oxide layer on the core material.

In the absence of the aging step a thinner and softer layer of metal oxide would be obtained since the metal oxide salt upon precipitation forms a gel layer of metal oxide which may disintegrate or erode upon washing or by mechanical stirring. In order to enable further growth of the metal oxide layer by further coating with additional layer/layers of metal oxide, the aging step is required.

The aging may be conducted at a temp of 4-90° C., preferably at 15-60° C. and most preferably the aging is conducted at a temperature 20° C.-40° C.

Thus the repeated steps of coating and aging also enable the growth of thicker and stronger layer of metal oxide.

As used herein, the term "metal oxide layer" encompasses the product of both a single processing step as well as a product of a process in which the initially coated particles are further processed, by the optional further processing steps, described above.

Preferably the positive zeta potential in step (a) is less than +150 mV, more preferably zeta potential in the range +60 mV to +130 mV. The preferred zeta potential in step (d) is less than +150 mV, more preferably in the range +5 mV to +130 mV, and most preferably +100 mV to +100 mV. This is the preferred zeta potential also in the further, optional, processing steps.

The water insoluble particulate matter may be a pharmaceutically, cosmetically, or agrochemical active ingredient.

Preferably the water insoluble particulate matter is a dermatological active agent.

Preferably the dermatological active agent is selected from antifungal agents, antibacterial agents, antiinflammatory agents, antipruritic agents, anti psoriatic agent, and anti acne agents. The dermatological agent may also be combinations of any of the above agents.

The antibacterial agents may be a bacteriostatic or bacteriocidal drug.

The dermatological active agent may be for example antifungal agents such as ketoconazole, bacteriostatic drugs such as metronidazole or erythromycin, bactericidal drugs such as bacitracin, corticosteroids such as mometasone furoate, methylprednisolone aceponate, prednicarbate, triamcinolone acetonide, fluocinonide, desoximetasone, bethasone valerate or mometasone furoate, antipruritic agent such as doxepin hydrochloride, and anti acne agents such as benzoyl peroxide, azelaic acid, retinoids such as tretinoin (retinoic acid) or adapalene.

More preferably the anti-acne agent is selected from benzoyl peroxide, retinoid, and mixtures thereof.

Most preferably the anti-acne agent is benzoyl peroxide.

According to another preferred embodiment of the present invention the particulate matter is a pesticide.

The pesticides may be for example a herbicide, an insecticide, a fungicide, and mixtures thereof.

The herbicide may be selected from thiocarbamate herbicides, haloacetanilide herbicides, nitroaniline herbicides, and mixtures thereof.

The insecticide may be for example an organophosphorus insecticides, a pyrethroid insecticides, a neonicotinoid insecticide, and mixtures thereof.

The pesticides may be for example thiocarbamate herbicides such as butylate, cycloate, molinate, or vemolate; haloacetanilide herbicides such as acetochlor, metolachlor, alachlor, butachloror propachlor; nitroaniline herbicides such as trifluralin, organophosphorus insecticides such as parathion, malathion, or fonofos; pyrethroid insecticides such as bifenthrin, permethrin, lambda-cyhalothrin, deltamethrin, tralomethrin, cypermethrin, or tefluthrin; carbamate insecticides such as aldicarb; Neonicotinoid insecticides such as imidacloprid or thiamethoxam; and fungicides such as azoxystrobin, kresoxim-methyl, epoxiconazole, captan, folpet, mancozeb, carbendazim, chlorothalonil, fenpropidin or tebuconazole.

Preferably the metal oxide is selected from Silica, Titania, Alumina, Zirconia, ZnO, and mixtures thereof. Most preferably the metal oxide is silica.

The metal oxide salt is preferably an alkali metal oxide salt.

According to a preferred embodiment of the present invention the metal oxide salt is selected from sodium silicate, potassium silicate, sodium aluminate, potassium aluminate, sodium titanate, potassium titanate, sodium zirconate, potassium zirconate, and mixtures thereof. Most preferably the metal oxide salt is a silicate salt.

Further according to a preferred embodiment of the present invention the cationic additive (i.e. first and/or second cationic additive) is selected from a cationic surfactant, a cationic polymer, and mixtures thereof. Most preferably the first cationic additive is a cationic surfactant, and the second cationic additive is a cationic polymer.

The first cationic additive is preferably a cationic surfactant.

Preferably the cationic surfactant selected from monoalkylquaternary ammonium salts, dialkyl quaternary ammonium salts, and mixtures thereof.

Preferably the monoalkylquaternary ammonium salts are selected from benzethonium chloride, benzalkonium chloride, cetyltrimethylammonium chloride (CTAC), cetyltrimethylammonium bromide (CTAB), lauryltrimethylammonium chloride, stearyltrimethylammonium chloride, cetylpyridinium chloride, and mixtures thereof.

Most preferably the monoalkylquaternary ammonium salt is cetyltrimethylammonium chloride.

Preferably the dialkyl quaternary ammonium compound is distearyldimethylammonium chloride.

Additional cationic surfactants which can be used are described in: John A. Wenninger et al. (Editors) *International Cosmetic Ingredient Dictionary and Handbook* (Eighth Edition 2000), Vol. 2 pp. 1140-1147, Published by The cosmetic, Toiletry, and Fragrance Association, incorporated herein by reference in its entirety.

Preferably the weight ratio of the first cationic additive to the water-insoluble particulate matter is in the range 1:1000-1:10, more preferably 1:200-1:50, most preferably about 1:100.

The second cationic additive may be a cationic polymer, a cationic surfactant or mixtures thereof. The cationic surfactant may be as described above.

According to a preferred embodiment of the present invention the second cationic additive is a cationic polymer.

Preferably the weight ratio of the second cationic additive to the first coated particulate matter is in the range 1:1000-1:10, more preferably 1:200-1:50, most preferably about 1:100.

Preferably the weight ratio of the second cationic additive to the further processed coated particulate matter (e.g. second coated particulate matter) is in the range 1:1000-1:10, more preferably 1:200-1:50, most preferably about 1:100.

Preferably the cationic polymer (of the first cationic additive or second cationic additive) is selected from poly(ethyleneimine) (PEI), poly(dimethyldiallylammonium chloride) (PDAC), poly(acrylamide-co-diallyl-dimethylammonium chloride) (polyquaternium-7), poly(allylamine hydrochloride) (PAH), Chitosan, polylysine, and mixtures thereof.

According to another preferred embodiment of the present invention the second cationic additive is selected from colloidal alumina, colloidal ceria (CeO2), colloidal alumina coated silica (such as Ludox CL, Sigma-Aldrich), and mixtures thereof.

The second cationic additive may be a colloidal metal oxide bearing a positive charge such as described above (e.g. colloidal alumina, colloidal ceria (CeO2), colloidal alumina coated silica, or mixtures thereof).

Further according to a preferred embodiment of the present invention, the process further comprising drying the obtained coated particulate matter.

Still further according to a preferred embodiment of the present invention, the drying is by a method selected from spray drying, lyophilization, oven drying, vacuum drying, and fluidized bed.

Additionally, according to a preferred embodiment of the present invention, the process further comprising chemically modifying the surface of the coated particulate matter.

The surface chemical modification preferably comprises modifying the metal oxide surface with organic groups, preferably hydrophobic groups.

Preferably process comprising attaching hydrophobic groups to the surface of the metal oxide layer.

The hydrophobic groups may be for example an alkyl silane, dialkyl silane, trialkyl silane, (such alkyl groups may be further substituted with one or more fluoro atoms), aryl silane (such as benzyl silane, or phenyl silane), diaryl silane, or triaryl silane.

Moreover according to a preferred embodiment of the present invention, the chemical surface modification comprises reacting silanol groups on the surface of the metal oxide layer with precursors selected from monohalotrialkyl silane such as chlorotrimethylsilane, dihalodialkyl silane such as dichlorodimethyl silane, trihaloalkyl silane such as trichloromethylsilane, monoalkoxytrialkyl silane such as methoxy tri methyl silane, dialkoxydialkyl silane such as dimethoxydimethylsilane, trialkoxyalkyl silane such as trimethoxymethylsilane, aryltrihalosilane such as phenyltrichlorosilane, diaryldihalosilane such as diphenyldichlorosilane, triarylhalosilane such as triphenylchlorosilane, aryltrialkoxysilane such as phenyltrimethoxysilane, diaryldialkoxysilane such as diphenyldimethoxysilane, triarylalkoxysilane such as triphenylmethoxysilane, and mixtures thereof.

Preferably the alkyl group includes 1-18 carbon atoms, more preferably 1-6 carbon atoms. Most preferably the alkyl is methyl. The alkyl groups may be substituted by one or more fluoro atoms. Preferably the alkoxy group includes 1-6 carbon atoms and more preferably 1-2 carbon atoms.

The halo group may be for example chloro, bromo, iodo, fluoro. Most preferably the halo groups are chloro and bromo.

The aryl is preferably phenyl or benzyl.

The precursors react with the silanol groups on the surface of the metal oxide layer to form a siloxane bond.

The attachment of the hydrophobic groups to the surface of the metal oxide layer can be performed by reacting the dried coated particulate matter with the above precursors. The procedure for attaching hydrophobic groups to the metal can be conducted as follows: a dried powder of coated particulate matter is suspended in an organic solvent such as toluene. A precursor (hydrophobization reagent) from the list above such as dimethyldichlorosilane is added to the organic phase (mixture), optionally in the presence of a halogen scavenger such as trialkyl amine or triethanol amine. The organic mixture is refluxed for at least about 24 hours to obtain coverage of the metal oxide layer with the hydrophobic groups via attachment of the hydrophobic groups to the silanol groups on the surface of the metal oxide layer.

Preferably the particulate matter is a pesticide as described above, said metal oxide is silica, and said metal oxide surface is modified using a precursor described above, preferably dialkyldihalo silane, and most preferably dimethyldichloro silane.

Most preferably the insecticides (Neonicotinoid insecticides) is imidaclopride or thiamethoxam.

Further according to a preferred embodiment of the present invention the obtained metal oxide coating layer has a width (thickness) of 0.3 micron or above, preferably 0.3-10 micron.

The width of the metal oxide layer may be determined for example by a Transmission Electron Microscope or Confocal Microscope such that in a circular cross sectional area of the particle the smallest width is at least 0.3 micron (the width is determined as the smallest distance from the surface of the particle (i.e. metal oxide surface) to the core-metal oxide interface).

As mentioned above, step (d) may be repeated one or more additional times.

Thus, for example in case step (d) in the process is repeated one additional time, the process preferably comprises:

(a) contacting the solid, water-insoluble particulate matter, with a first cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon;

(c) aging said coating layer to obtain first coated particulate matter;

(d) contacting the first coated particulate matter with a second cationic additive in an aqueous medium to obtain a dispersion of said first coated particulate matter having a positive zeta potential;

(e) coating the first coated particulate matter by precipitation of a metal oxide salt onto the surface of the particulate matter, forming a metal oxide layer thereon;

(f) aging said coating layer to obtain second coated particulate matter;

(g) coating the solid, water-insoluble particulate matter, by precipitation of a metal oxide salt onto the surface of the second coated particulate matter, forming a metal oxide layer thereon; and (h) aging said coating layer to obtain third coated particulate matter.

According to a preferred embodiment the process of the present invention comprises:

(a) contacting the solid, water-insoluble particulate matter, with a first cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon; and, preferably said coating comprising adding a metal oxide salt to reach a value of pH 7-11; and acidifying to obtain a pH value of 1-3, said coating is repeated one additional time.

(c) separating the coated particulate matter from the dispersing aqueous medium and rinsing and redispersing the obtained coated active ingredient in an aqueous medium;

(d) aging said coating layer to obtain first coated particulate matter;

(e) contacting the first coated particulate matter with a second cationic additive in an aqueous medium to obtain a dispersion of said first coated particulate matter having a positive zeta potential and further processing the dispersion through steps (b)-(d) to obtain a further processed coated particulate matter.

Preferably steps (b)-(d) are further processed one or two additional times, more preferably two additional times (i.e. steps (b)-(d) are processed totally 3 times)

More preferably step (b) comprising adding a metal oxide salt to reach a value of pH 8-10; and acidifying to obtain a pH value of 1-3, said coating is repeated one additional time.

For certain active agents such as acidic compounds it may be preferable to add a metal salt to reach a value of pH 7-8; and acidifying to obtain a pH value of 1-3, said coating is repeated one additional time.

Step (b) may further comprise adjusting the pH of the dispersion obtained in (a) to a value between 5.5-8 before coating.

The invention additionally relates to the coated particulate matter obtained by the processes as described in the present invention.

According to a preferred embodiment of the present invention the particles (coated particulate matter) have a diameter of 0.5-100 micron. More preferably the diameter of the particles is in the range 1-50 micron and most preferably in the range 5-30 micron.

The particles may be useful for cosmetic or medical applications.

The particles may also be used in agricultural or polymeric industry.

The particles may be useful for any application wherein the active ingredient should be isolated, temporally or permanently from the ambient surroundings.

It is appreciated that the particles of the present invention are composed of distinct regions of the metal oxide layer and the core material (i.e. the water insoluble particulate matter). The particles are preferably characterized in that the core material is substantially free of the metal oxide and further in that the metal oxide layer is substantially free of said core material, e.g. either as particle dispersion (in the nanometric range of below 0.1 micron) of the water insoluble particulate matter or as molecular dispersion of said water insoluble particulate matter. Thus, according to a preferred embodiment of the present invention the metal oxide layer is substantially free of core material (either as molecules or as nanometric particles). The term "substantially free" in this context denotes that the concentration of the molecules of the core material or the concentration of the nanometric particles of the core material is negligible as compared to the metal oxide. Similarly, by the term "the core material is substantially free of the metal oxide" is meant that the concentration of the metal oxide in the core, is negligible as compared to the core material.

The invention further relates to a pharmaceutical, cosmetic or cosmeceutical composition for topical administration comprising a carrier; and a plurality of particles, each of said particles comprising a solid, water insoluble dermatologically active agent, coated by a metal oxide layer.

The carrier may be a cosmetic or pharmaceutically acceptable carrier. The coated dermatologically active agent is preferably dispersed in the carrier.

The coated dermatological active agent may be easily dispersed or suspended in a carrier or diluent.

Simple mixing with any suitable mixer or carrier is sufficient to achieve an effective dispersion. If necessary, high shear forces may be applied to facilitate fast and efficient mixing of the coated particles in the carrier.

The particles are preferably non-leaching when dispersed in a carrier, and most preferably non-leaching in an aqueous-based carrier.

By the term "non-leaching" it is meant that the leaching of the particulate matter (active agent) from the particles into an aqueous-based carrier is less than 1% w/w (this value refers to the concentration of the active agent in the aqueous carrier), preferably less than 0.5% w/w and most preferably less than 0.1% w/w at room temperature (20° C.), under gentle agitation for 1 hour or until a steady state concentration is achieved. Most preferably the leaching into an aqueous-based carrier refers to water.

The metal oxide coating of the present invention is highly advantageous since it is capable of isolating the solid, water insoluble particulate matter from its surrounding medium, and yet enables the release the particulate matter upon application to the surface to be treated.

Preferably the dermatological active agent is selected from antifungal agents, antibacterial agents, antiinflammatory agents, antipuritic agents, anti psoriatic agent, anti acne agents, and mixtures thereof.

Preferably the anti-acne agent is selected from benzoyl peroxide, a retinoid, and mixtures thereof.

Preferably the retinoid is retinoic acid or adapalene.

Most preferably the anti-acne agent is benzoyl peroxide.

Benzoyl peroxide (BPO) is particularly preferred compound for coating with a metal oxide. The purpose of the BPO coating is to provide at least one of the following benefits: a) to reduce the skin irritation of the BPO crystals, b) to significantly reduce side effects caused by BPO in topical formulations, c) to increase the dispersability of BPO crystals in aqueous solutions in the absence of surfactant, d) to prevent direct contact of the BPO crystals from the skin, e) prevent additional crystal growth processes of BPO after grinding, f) to increase the stability of the BPO, g) to have good compatibility with other ingredients in the formulation, h) to produce a sustained release mechanism of BPO onto the skin.

According to a preferred embodiment of the present invention, the metal oxide is selected from Silica, Titania, Alumina, Zirconia, ZnO, and mixtures thereof. Most preferably the metal oxide is silica.

Additionally, according to a preferred embodiment of the present invention, the particles of the coated particulate matter has a surface area of 20-400 $m^2/g$, preferably 50-250 $m^2/g$ and most preferably 80-180 $m^2/g$.

Further according to a preferred embodiment of the present invention, the weight ratio of said metal oxide to said solid, water-insoluble particulate matter, is in the range 3:97 to 50:50. The weight ratio of the metal oxide layer to the solid, water-insoluble particulate matter, may be also in the range 5:95 to 50:50, 10:90 to 50:50, 5:95 to 30:70, or 10:90 to 30:70.

Still further according to a preferred embodiment of the present invention, the weight ratio of said metal oxide to said solid, water-insoluble particulate matter, is in the range 10:90 to 20:80.

Moreover according to a preferred embodiment of the present invention, the particles (coated particulate matter) have a diameter of 0.5-100 micron.

Additionally according to a preferred embodiment of the present invention, the thickness of said metal oxide layer is in the range 0.3-10 micron.

The invention additionally relates to a composition for topical administration comprising:
- a plurality of particles, each of said particles comprising
  - a solid, water insoluble dermatologically active agent, coated by a metal oxide layer; and
- a carrier;
- said composition having reduced side effects and at least essentially the same therapeutic effect as compared to a reference composition; the difference between said composition and the reference composition being in that in the latter the active agent is not coated.

The concentration of the coated solid, water insoluble dermatological active agent, in the composition may or may not be the same as that of the dermatological active agent in the reference composition.

As used herein the term "therapeutic effect" means providing therapeutic benefit in the treatment, prevention or management of one or more skin conditions. Thus, the term "therapeutic effect" is used herein in a broad sense and includes also prophylactic effects.

The term "therapeutic effect" also means antagonizing or inhibiting activities associated with a patient's surface body disease or disorder such as skin's inflammatory processes, psoriasis, puritis, etc., hence providing subjective relief of symptoms or objectively identifiable improvement as noted by the clinician or other qualified observer.

The amount of the active agent in the composition should be therapeutically effective amount to provide the desired therapeutic effect, namely an amount which is effective to achieve the intended purpose without undesirable side effects (for example toxicity, irritation or allergic response).

According to a preferred embodiment of the present invention, the carrier is a cosmetic or pharmaceutical carrier.

The carrier may be in the form of ointment, a cream, a lotion, an oil, an emulsion, a gel, a paste, a milk, an aerosol, a powder, a foam, a wash. Most preferably the carrier is in the form of a gel or a cream more preferably oil-in-water cream. Most preferably the dispersing phase (i.e. the carrier) is aqueous based and comprises water as dispersing medium.

Additionally according to a preferred embodiment of the present invention, the composition is for the treatment of a disease or condition selected from acne, infection, inflammation, puritis, psoriasis, seborrhea, contact dermatitis, rosacea, and a combination thereof.

Further according to a preferred embodiment of the present invention, the dermatological agent is selected from antifungal agents, antibacterial agents, antiinflammatory agents, antipuritic agents, anti psoriatic agent, and anti acne agents.

The antifungal agents, antibacterial agents, antiinflammatory agents, antipuritic agents, anti psoriatic agent, and anti acne agents may be as described in the present invention above.

Most preferably the dermatological active agent is an anti-acne agent.

Moreover according to a preferred embodiment of the present invention, the anti acne agent is selected from benzoyl peroxide, retinoid, and mixture thereof.

Most preferably the anti-acne agent is benzoyl peroxide.

According to a preferred embodiment of the present invention the anti-acne agent is benzoyl peroxide and the side effect is selected from irritation, erythema, stinging, scaling, dryness, and any combination thereof.

According to a preferred embodiment of the present invention the dermatological agent is benzoyl peroxide and said side effects are irritation, erythema, scaling, dryness, and stinging.

Additionally according to a more preferred embodiment of the present invention, the dermatological agent is an anti-acne agent yielding a therapeutic effect manifested in a colony reduction of *P. Acnes* (*Propionibacterium acnes*).

Further according to a preferred embodiment of the present invention, the therapeutic effect is at least a 0.5 logarithmic colony reduction of *P. acnes* in at least 90% of the subjects treated.

Further according to a preferred embodiment of the present invention, the therapeutic effect is at least 1 logarithmic colony reduction of *P. acnes* in at least 60% of the subjects treated. More preferably the therapeutic effect is at least 1 logarithmic colony reduction of *P. acnes* in at least 80% of the subjects treated.

Preferably said colony reduction of *P. acnes* occurs within 2 weeks of treatment.

Preferably said colony reduction of *P. acnes* occurs within 4 weeks of treatment.

Most preferably the anti acne agent is benzoyl peroxide.

Moreover according to a preferred embodiment of the present invention, the anti acne agent is benzoyl peroxide, the therapeutic effect is a described above and the side effects are irritation, erythema, scaling, dryness, and stinging.

According to a preferred embodiment of the present invention the metal oxide is selected from Silica, Titania, Alumina, Zirconia, ZnO, and mixtures thereof.

Additionally according to a preferred embodiment of the present invention, the weight ratio of said metal oxide to said solid, water-insoluble dermatological active agent, is in the range 3:97 to 50:50. The weight ratio of the metal oxide layer to the solid, water-insoluble particulate matter, may be also in the range 5:95 to 50:50, 10:90 to 50:50, 5:95 to 30:70, 10:90 to 30:70.

Further according to a preferred embodiment of the present invention, the weight ratio of said metal oxide to the solid, water-insoluble particulate matter, is in the range 10:90 to 20:80.

Moreover according to a preferred embodiment of the present invention, the particles have a diameter of 0.5-100 micron. Preferably the particles have a diameter of 0.8-100 micron, more preferably 1-50 micron and most preferably 5-30 micron.

Additionally according to a preferred embodiment of the present invention, the thickness of said metal oxide layer is in the range 0.3-10 micron. More preferably 0.3-3 micron, and even more preferably 0.3-1 micron. The thickness of the metal oxide layer may also be in the range 0.5 to 3 micron, and most preferably 0.5 to 2 micron.

According to a preferred embodiment of the present invention, the carrier is in the form of an ointment, a cream, a lotion, an oil, an emulsion, a gel, a paste, a milk, an aerosol, a powder, a foam, or a wash.

The invention additionally relates to a method for treating a surface condition in a subject, comprising topically administering onto the surface a composition as described in the present invention.

The invention further relates to a method for treating a surface condition in a subject, comprising topically administering onto the surface a composition comprising coated particulate matter obtained by the process described in the present invention.

Preferably the subject is a mammal, and most preferably the mammal is a human.

The term "treating" or "treatment" as used herein includes any treatment of a condition (disease or disorder) associated with a patient's body surface such as the skin or mucosal membrane, and includes inhibiting the disease or disorder (i.e. arresting its development), relieving the disease or disorder (i.e. causing regression of the disease or disorder), or relieving the conditions caused by the disease (i.e. symptoms of the disease). The concentrations of the dermatological agents that can be used for treatment of a specific disease or disorder may be as described in The Merck index an encyclopedia of chemical, drugs, and biologicals/The Merck index an encyclopedia of chemical, drugs, and biologicals. Rahway, N.J.; Merck & Co; 1989., incorporated herein by reference in its entirety.

Although individual needs may vary, determination of optimal ranges for effective amounts of the compositions is within the skill of the art. Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s).

According to a preferred embodiment of the present invention, the surface of a subject body is skin or mucosal membrane.

According to a preferred embodiment of the present invention, the metal oxide layer releases the particulate matter following topical application (administration).

Preferably the coated particulate matter is characterized by having a surface area in the range of 20-400 $m^2/g$, preferably 50-250 $m^2/g$ and most preferably 80-180 $m^2/g$.

Preferably the water insoluble particulate matter is a dermatological active agent as described above in the present invention, more preferably an anti-acne agent, and most preferably the water insoluble particulate material is benzoyl peroxide.

According to another preferred embodiment the solid, water insoluble particulate matter, is a retinoid.

Without being bound to theory it is assumed that benzoyl peroxide is released from the particles through the metal oxide coating layer by extraction by lipids available on the skin. Upon application on the skin, it is assumed that the skin lipids diffuse through the metal oxide layer and extract the benzoyl peroxide present in the core. Other dermatological agents may be similarly released from the particles.

The invention additionally relates to the use of coated particulate matter, the particulate matter being a solid, water-insoluble topically dermatologically active agent, coated by a metal oxide layer, for the preparation of a medicament for topical administration on the skin or mucosal membrane.

The invention further relates to the use of coated particulate matter according to the process described in the present invention, the particulate matter being a topically dermatologically active agent, for the preparation of a medicament for topical administration on the skin or mucosal membrane.

The topical administration is preferably for treating a disease or disorder selected from acne, psoriasis, seborrhea, rosacea contact dermatitis, infection, inflammation, puritis, and any combination thereof.

The invention further relates to compositions for pest control comprising a pesticide, said pesticide being a solid, water-insoluble particulate matter, coated by a metal oxide layer.

Moreover the invention relates to compositions for pest control comprising coated particulate matter obtained by the process described in the present invention, said particulate matter being a pesticide.

Coating pesticides with a metal oxide layer is highly advantageous. The motivation for metal oxide coating of pesticides is to have the toxicity, in nearly all categories, reduced compared to the uncoated product. The coating can also be used for other properties like extend residual control (prolong duration of action), reduce phytotoxicity and retard volatility. Over the years, authorities have limited the use of pesticides due to severe environmental pollution. One of the ways to reduce the amount of pesticides used in the field is to encapsulate (coat) it and to control it's release to the ground. In that case smaller amounts of pesticides will be used for longer period of time having the same bioefficacy but reduced environmental hazardous. The added value of silica coating of pesticides is the perfect tolerability silica has with the environment since most soils contain large amounts of silica.

The compositions may be used for treatment of plants and soil.

According to a preferred embodiment of the present invention, the compositions are for use in crop protection.

The pesticides may be for example a herbicide, an insecticide, a fungicide, and mixtures thereof.

The herbicide may be selected from thiocarbamate herbicides, haloacetanilide herbicides, nitroaniline herbicides, and mixtures thereof.

The insecticide may be for example an organophosphorus insecticides, a carbamate insecticide, a pyrethroid insecticides, Neonicotinoid insecticides, and mixtures thereof.

The pesticides may be for example thiocarbamate herbicides such as butylate, cycloate, molinate, or vernolate; haloacetanilide herbicides such as acetochlor, metolachlor, alachlor, butachloror propachlor; nitroaniline herbicides such as trifluralin, organophosphorus insecticides such as parathion, malathion, or fonofos; pyrethroid insecticides such as bifenthrin, permethrin, lambda-cyhalothrin, deltamethrin, tralomethrin, cypermethrin, or tefluthrin; carbamate insecticides such as aldicarb; Neonicotinoid insecticides such as imidacloprid or thiamethoxam and fungicides such as azoxystrobin, kresoxim-methyl, epoxiconazole, captan, folpet, mancozeb, carbendazim, chlorothalonil, fenpropidin, or tebuconazole.

More preferably the pesticide is and insecticide selected from imidacloprid, thiamethoxam, bifenthrin, aldicarb, and any combination thereof.

Further according to a preferred embodiment of the present invention, the metal oxide is selected from Silica, Titania, Alumina, Zirconia, ZnO, and mixtures thereof.

Moreover according to a preferred embodiment of the present invention, the weight ratio of the metal oxide to said solid, water-insoluble particulate matter, is in the range 3:97 to 50:50.

Additionally according to a preferred embodiment of the present invention, the weight ratio of the metal oxide to said solid, water-insoluble particulate matter, is in the range 10:90 to 20:80.

Further according to a preferred embodiment of the present invention, the particles have a diameter of 0.5-100 micron.

Moreover according to a preferred embodiment of the present invention, the thickness of the metal oxide layer is in the range 0.3-10 micron.

According to another preferred embodiment of the present invention the compositions further comprising organic groups, preferably hydrophobic groups attached to the surface of the metal oxide layer.

Preferably the hydrophobic groups are selected from alkyl silane, dialkyl silane, trialkyl silane, (such alkyl groups may be further substituted with one or more fluoro atoms), aryl silane (such as benzyl silane, or phenyl silane), diaryl silane, triaryl silane, and mixtures thereof.

The definitions of the alkyl and aryl groups are as described above with respect to the process.

The purpose of attaching hydrophobic groups to the surface of the metal oxide layer is to control (i.e. to hinder) the water penetration rate into the particles and consequently to control the release of the pesticide from the particles. Modifying the surface of the metal oxide layer by hydrophobic groups enables to control the release of the pesticide from the particles in a manner that matches the need for the pesticide and at the desired rate.

Preferably the insecticide is imidacloprid. More preferably the insecticide is imidacloprid and said alkyl silane or dialkyl silane is methyl silane, or dimethyl silane.

The amounts of pesticides that can be used for a specific application, can be found in guidelines issued by the ministry of agriculture in each country.

Preferably the compositions for pest control described above may further comprise a carrier, wherein said coated water-insoluble particulate matter is dispersed in said carrier.

Thus, the metal oxide coated pesticide of the present invention may be employed per-se or in the form of mixtures with a solid, semi solid or liquid dispersible carrier vehicles and/or other known compatible active agents such as other pesticides, or fertilizers, growth-regulating agents, etc., if desired, or in the form of particular dosage preparations for specific application made therefrom, such as solutions, emulsions, suspensions, powders, pastes, foams, tablets, polymeric sheets, aerosols, etc. and which are thus ready for use.

The particles, composed of a solid, water-insoluble particulate matter, being a pesticide coated by a metal oxide layer may be characterized by additional features as described above in the present invention with respect to the process.

EXAMPLES

In the examples below, all % values referring to a solution are in (w/w).
All % values, referring to dispersions are in (w/w).
All solutions used in the example below refer to an aqueous solution of the indicated ingredient.

Example 1: Coating Procedure for BPO Crystals (Triple Double)

A. Milling Step 3000 g of BPO 75% wet cake (75% BPO and 25% water) (Benzoyl Peroxide) USP grade (Farchemia, Italy) were weighted. A solution of 8250 g 0.25% CTAC (cetyltrimethylammonium chloride) was added to an inline high shear system (IKA LABOR PILOT). The CTAC solution was stirred by a mechanical stirrer (900 rpm) while the inline system was working at 13700 rpm. The BPO wet cake was slowly added to the container. The milling process was stopped at BPO crystals size of d0.9<40 μm (Malvern Mastersizer 2000). The dispersion weight was 11300 g with 20.5% solids having positive surface charge (ζ potential of +114.9 mV).

B. First Coating Step

The dispersion after milling was transferred into 18 L container under stirring with a mechanical stirrer. The dispersion pH was adjusted to 7.5 with 5M NaOH solution. 4% sodium silicate solution was slowly added to obtain pH=10.00. Then the pH was reduced to pH 2 by addition of 1M HCl solution. A second coating step was taking place by adding 4% sodium silicate solution to obtain pH=10, followed by acidification with 1M HCl to pH=2. The pH of the dispersion was adjusted to 8.58 using 5M NaOH solution. The ζ potential (zeta potential) after the coating was (−37.0) mV and the solids content was 16.67% out of which BPO assay (by HPLC) was 16.00%.

C. Aging Step

The silica coated BPO dispersion was kept under stirring at room temperature for 45 h for aging. After 24 h the pH was adjusted to 8.0 with 5M NaOH solution.

D. Washing Step

Separation and washing were done by filtration on a buchner funnel. The cake was washed five times with RO (Reverse Osmosis) water. The overall wet cake weight was 4200 g. The cake was dispersed with in 1800 g RO water to obtain 6000 g silica coated dispersion.

E. Addition of Polycation

The dispersion pH was adjusted to 8.35 using 9 g of 5 M NaOH. 4000 g of 0.5% polyquaternium-7 (poly(acrylamide-co-diallyl-dimethylammonium chloride)) were added to the BPO dispersion under vigorous stirring. ζ potential was +24.7 mV and BPO assay −21.39%.

F. Second Coating

4% sodium silicate solution were added slowly to the dispersion to obtain pH=10. 1M HCl solution was added to obtain pH=2. A second portion of 4% sodium silicate solution was added to obtain pH=10. 1M HCl were added to obtain pH=2. The pH of the dispersion was adjusted to 8.5 using 5M NaOH solution. The ζ potential after the second coating was (−20.7) mV.

G. Aging

The silica coated BPO dispersion was allowed to stay under stirring at room temperature for 44 h of aging. After 24 h the pH was readjusted to 8.4 with 5M NaOH solution. After aging the pH was 7.2 and the ζ potential was (−24.2) mV.

H. Washing

The washing was done in the same way as in paragraph d.

I. Addition of Opposite Charge Polymer

The pH of the dispersion was adjusted to 8.33 using 10.9 g of 5 M NaOH. Polyquaternium-7 (poly(acrylamide-co-diallyl-dimethylammonium chloride)) solution was added under vigorous stirring to the coated BPO dispersion up to a final concentration of 0.3%. The ζ potential was +22.9 mV and BPO assay was 13.00%.

J. Third Coating

4% sodium silicate solution were added slowly to the dispersion to obtain pH=10. 1M HCl solution was added to obtain pH=2. A second portion of 4% sodium silicate solution was added to obtain pH=10. 1M HCl were added to obtain pH=2. 5M NaOH were added to adjust the pH to 8.60. The ζ potential after the second coating was (−25.7) mV.

K. Washing

The washing was done in the same way as in paragraph d.

L. Final Product

RO water was used to disperse the wet cake to obtain coated BPO dispersion having a BPO assay of 18.98%.

Example 2: BPO Coating without Polycation

A. Milling Step

BPO USP grade, wet cake (75% BPO and 25% water, Aldrich, USA) were added to an 0.3% CTAC (cetyltrimethylammonium chloride) solution. The BPO/CTAC dispersion was milled until the BPO particle size was d0.9<40 micron. The ζ potential was +122.0 mV.

B. First Coating Step

The pH of the dispersion was adjusted to 7.2 using 5M NaOH solution. 4% sodium silicate solution was slowly added to the BPO dispersion to obtain pH=10. The dispersion pH was reduced to pH 2.12 by addition of 1M HCl solution. A second coating step was done by adding 4% sodium silicate solution to obtain pH=10, followed by acidification with 1M HCl to pH 2. The pH of the dispersion was adjusted to 8.15 using 5M NaOH solution. The ζ potential after the coating was (−41.6) mV.

C. Aging and Washing Steps

The silica coated BPO dispersion was kept under stirring at room temperature for 48 h aging. After 24 h the pH was adjusted to 8.84 using 5M NaOH solution. The separation of the solids and the washing step was operating by filtration on a buchner funnel. The wet cake was washed five times with RO water.

D. Second Coating

After washing the pH of the dispersion was adjusted to 8.00. 4% sodium silicate solution were added slowly to the dispersion to obtain pH=10. 1M HCl solution was added to obtain pH=2. A second portion of 4% sodium silicate solution was added to obtain pH=10. 1M HCl were added to obtain pH=2. 5M NaOH solution was added to adjust the pH to 8.16. The ζ potential after the second coating was −30.3 mV.

E. Aging and Washings

The silica coated BPO dispersion was kept under stirring at room temperature for 48 h of aging. After 24 h the pH was adjusted to 8.15 using 5M NaOH solution. Washing was done by filtration in the same way as in paragraph C.

F. Third Coating

4% sodium silicate solution was added slowly to the dispersion to obtain pH 10. 1M HCl solution was added to obtain pH=2. A second portion of 4% sodium silicate solution was added to obtain pH=10. 1M HCl was added to obtain pH=2. 5M NaOH was used to adjust the pH to 8.03.

G. Aging and Washing

The aging period was 72 h, with pH corrections to 8 every 24 h. The dispersion was separated by filtration and washed three times with RO water.

H. Final Product

RO water was used to disperse the coated BPO wet cake. The ζ potential was −14.6 mV.

Example 3: Benzil Coating (Double Coatings)

A. Milling Step 20 g of Benzil (Aldrich, USA) were suspended in 180 g 0.2% CTAC solution to obtain 10% solids dispersion. The dispersion was first mixed with high shear homogenizer at 3000 rpm for 5 min. The dispersion was milled in M-110Y microfluidizer processor (Microfluidics) for one pass at 15,000 psi. The Benzil particle size after milling was d(0.9)=21.83 μm. ζ potential was +119.7 mV.

B. Coating Step

The pH of the dispersion was adjusted to 7.9. 4% of sodium silicate solution was added to obtain pH=10. 1M HCl solution was added to obtain pH=2. 4% sodium silicate solution was added again to obtain pH=9.88. 1M HCl added to obtain pH=2. The pH of the dispersion was adjusted to 7.96 using 1M NaOH solution.

C. Aging Step

The dispersion was stirred for 72 h with a mechanical stirrer. Every 24 h the dispersion pH was adjusted to 8.0.

D. Separation and Washings

Separation process was done by centrifugation (Survall RC 5c plus). The dispersion was transferred to centrifuge tubes and was separated at 3000 rpm for 6 min. The wet cake was washed with TDW (triple distilled water) and then separated in centrifuge (3000 rpm for 6 min) again. The wet cake was dispersed in TDW.

E. Polyquaternium-6 Addition

A solution of 140 g of 0.1% polyquaternium-6 was added to the Benzil dispersion. The dispersion was kept under stirring for 30 min before coating.

F. Second Coating

The pH of the dispersion was adjusted to 7.50. 4% of sodium silicate solution was added to obtain pH=10. 1M HCl solution added to obtain pH=2. 4% sodium silicate solution was added again to the stirred dispersion to obtain pH=10. 1M HCl was added to obtain pH=2. The pH of the dispersion was adjusted to 8.11 using 1M NaOH solution.

G. Final Product

After aging period of 40 h including correction after 24 h to pH 8, the dispersion was centrifuged at 3000 rpm for 6 min. The wet cake was dispersed in TDW.

Example 4: 4,4'-Dibromobenzil Coating (Triple Coating)

A. Milling 10 g of 4,4'-Dibromobenzil (Aldrich, USA) were suspended in 90 g 0.2% CTAC. The dispersion was first mixed with high shear homogenizer (Polytron PT 6100 Kinematica) with dispersing aggregates PT-DA 6045/6 at 3000 rpm for 5 min. The dispersion then was milled in M-110Y microfluidizer processor (Microfluidics) in one pass at 15,000 psi.

B. First Coating pH was adjusted to 7.85 using 1M NaOH. The dispersion was stirred with a mechanical stirrer and 4% sodium silicate solution was added to obtain pH=10. 1M HCl solution was added drop wise to obtain pH=2. 4% sodium silicate solution were added again to the dispersion to obtain pH=10. 1M HCl was added to obtain pH=2. The pH of the dispersion was adjusted to 8.02 using 1M NaOH solution.

C. Aging and Washings

The dispersion was stirred for 24 h and then was separated by a centrifuge at 3000 rpm for 6 min. The wet cake was washed with TDW and separated again by centrifuge at 3000 rpm for 8 min. The wet cake was suspended in TDW.

D. Polyquaternium-1 Addition

A solution of 150 g of 0.05% polyquaternium-1 was prepared and added to the Bromo benzil dispersion. The dispersion was kept under stirring for 30 min before coating.

E. Second Coating

4% sodium silicate solution was added to obtain pH=10, 1M HCl solution was added to obtain pH=2. 4% sodium silicate solution were added again to obtain pH=10. 1M HCl solution added to obtain pH=2. The pH of the dispersion was adjusted to 8.14 using 1M NaOH prior to the aging step.

F. Aging and Washings

The dispersion was aged for 24 h with continuous stirring. The dispersion was then separated in centrifuge at 300 rpm for 8 min. The wet cake was dispersed in TDW and was separated again by centrifuge at 3000 rpm for 8 min. The wet cake was redispersed in TDW.

G. Polyquaternium-1 Addition

A solution of 233.5 g of 0.05% polyquaternium-1 was prepared and added to the dispersion. The dispersion was kept under stirring for 30 min before coating.

H. Third Coating

4% sodium silicate solution was added to obtain pH=10, 1M HCl solution was added to obtain pH=2. 4% sodium silicate solution were added again to obtain pH=10. 1M HCl solution was added to obtain pH=2. The pH of the dispersion was adjusted to 8.14 using 1M NaOH prior to the aging step.

I. Final Product

After aging period of 20 h, the dispersion was centrifuged at 3000 rpm for 6 min. The wet cake was redispersed in TDW.

Example 5: Bifenthrin Coating (an Insecticide)

A. Milling 20 g of Bifenthrin (Shenzhen, China) were dispersed in 80 g 0.3% CTAC solution. The dispersion was milled with high shear homogenizer (Polytron PT 6100 Kinematica) with dispersing aggregates PT-DA 6045/6 in 15000 rpm for 5 min. The crystals size after milling was d(0.9)<5 μm.

B. Coating

The pH of the dispersion was adjusted to 7.14 using 1M NaOH. 4% sodium silicate solution were added to the dispersion to obtain pH=10. 1M HCl were added to obtain pH=1.8. Another portion of 4% sodium silicate was added to obtain pH=10. 1M HCl was added to obtain pH=2.2. 5M NaOH solution was added for pH correction to 7.

C. Aging

The dispersion was aged for a period of 72 h. After 24 h the pH was adjusted to 8.2, after aging of 48 h to 7.84 and at the end the pH was corrected to 7.9. The sample was analyzed by high resolution SEM.

D. Washing

The dispersion was separated using a centrifuge at 600 rpm for 6 min and the wet cake was washed with TDW. The dispersion was centrifuged once again at the same conditions and the wet cake was redispersed in TDW.

Example 6: Coating of Metal Alloy (Bronze Pigment)

A. Dispersion in Cationic Surfactant 25.20 g of bronze flakes (Wolstenholme international England) having a gold color were dispersed by vigorous stirring in 225.73 g of 0.5% Benzalkonium Chloride solution. The $\zeta$ potential was measured to be +60.1 mV.

B. First Coating 9.3 g of 4% sodium silicate solution were slowly added to the dispersion to obtain pH=9. 33.8 g of 1M HCl solution was added to obtain pH=2.8. 255.22 g 4% sodium silicate were added to obtain pH=9. 1M HCl was added to obtain pH=1.65. Neutralization to pH 7.66 was done using 1M NaOH solution. The $\zeta$ potential of the dispersion was (−16) mv.

C. Aging and Washing

Aging was done for 48 h (including pH correction to 8 after 24 h) and the dispersion was separated in a centrifuge at 300 rpm for 6 min. The flakes were washed with TDW and separated again under the same conditions. The cake was suspended in TDW.

D. PDAC Addition

A 450 g of 0.2% PDAC (GENAMINE PDAC from Cognis) was added to the flakes and $\zeta$ potential was measured to be +37.9 mV.

E. Second Coating 73.05 g of 4% sodium silicate solution were slowly added to the dispersion to obtain pH=10.00. 158.8 g of 1M HCl solution was added to obtain pH=2.12. 1012.9 g 4% sodium silicate were added to obtain pH=10.5. 308.1 g 1M HCl was added to obtain pH=2.02. pH was adjusted to 8.55 with 5M NaOH solution. The $\zeta$ potential after the silica coating was (−23.8) mv.

F. Aging and Washing

The dispersion was kept for 48 h for aging without pH adjustment and was separated by filtration. The wet cake was washed three times with RO water. The wet cake was resuspended in water.

G. Second PDAC Addition 1200 g of 0.2% PDAC (same type as above) solution were added to the coated bronze flakes dispersion. The $\zeta$ potential was +29.1 mV.

H. Third Coating

The pH of the dispersion was adjusted to 7.70 using 1M HCl solution. 295.7 g of 4% sodium silicate solution was added to obtain pH=10.2. 416.7 g 1M HCl solution was added to obtain pH=1.8. 1390.6 g of 4% sodium silicate solution was added to obtain pH=7.80 and 335.5 g 1M HCl was added to obtain pH=2.40. The pH was adjusted to 7.15 using 5M NaOH solution.

I. Aging and Washing

After aging period of 72 h without pH adjustment, the dispersion was separated by filtration and the wet cake was washed three times with RO water.

J. Final Product

The wet cake was dried in the oven for three days at 120° C. to obtain yellow powder of silica encapsulated Bronze pigment.

Example 7: Coating of Thiamethoxam (an Insecticide)

A. Milling Step

15% dispersion of thiamethoxam in 0.3% CTAC solution is prepared. The dispersion is initially mixed with high shear homogenizer and then milled in M-110Y microfluidizer processor (Microfluidics) for 18 min at 15,000 psi to obtain particle size distribution of d90<5 micron.

B. Coating Step

The coating process is done in an ice bath at temperature <10° C. 10% sodium silicate solution is added to obtain pH=10. 5M HCl solution is added to obtain pH=2. The process is repeated once more using 10% sodium silicate and 1M HCl. The pH of the dispersion is adjusted to 8 using 5M NaOH solution.

C. Aging Step

The thiamethoxam dispersion is kept for aging for 48 h. pH correction to 8 using 1M NaOH solution is done after 24 h.

D. Drying Step

The dispersion is dried using a spray dryer (Niro MOBILE MINOR) with rotary atomizer having an inlet temperature of 250° C. and outlet temperature of 80° C.

Example 8: Retinoic Acid Coating

A. Milling Step 20 g of Retinoic acid (Shenzhen, China) were suspended in 80 g 0.3% CTAC solution. The dispersion was initially mixed with high shear homogenizer at 3000 rpm for about 3 min and then milled in M-110Y microfluidizer processor for 15 min at 15,000 psi.

B. First Coating

The pH of the dispersion was adjusted to 3.5. A 4% sodium silicate solution was added to obtain pH=7.00. 1M HCl was added to obtain pH=2.0. Another portion of 4% sodium silicate solution was added to obtain pH=7.0. 1M HCl solution was added to obtain pH=2. The pH was adjusted to 6.5 using 1M NaOH solution.

C. Aging and Washing

Same as the former examples (aging for 48 h and washing by filtration).

D. Addition of Polycation

Solution of 0.5% Polyquaternium-10 was added to the silica coated retinoic acid dispersion. The ζ potential was +15.3.

Further steps are exactly as described in example 1 section F-L

M. Drying

The dispersion was dried in a spray dryer (Niro MOBILE MINOR) with rotary atomizer (inlet temperature 150° C., outlet temperature 60° C.).

Example 9: Surface Modification of Coated Thiamethoxam

Dry powder of silica-coated thiamethoxam (produced according to example 7) is dried at 110° C. for 24 h in an oven. The dry powder is suspended in dry toluene. The dispersion is stirred gently under inert atmosphere and brought to boiling point. dimethyldimethoxy silane is added drop-wise to the boiling dispersion under reflux conditions for 24 h. After the reflux the powder is separated by filtration and washed twice with methanol and once with hexane. The wet powder is dried in an oven for several hours. The resulting product is highly hydrophobic and will have reduced leaching to water.

Example 10: Background

*Propionibacterium acnes* (*P. acnes*) is the most common gram-positive microaerophilic organism found on normal skin. Although it has no intrinsic pathogenicity, *P. acnes* is believed to play a major role in the pathogenesis of acne. Most presently available topical anti-acne preparations such as benzoyl peroxides and topical antimicrobials exert their therapeutic effect through inhibition of *P. acnes* in vivo as demonstrated by a 1.0 to 2.0 logarithmic colony reduction.

Study Objective:

The purpose of the investigations was to evaluate and compare the topical inhibitory effect of two anti-acne preparations on *P. acnes* levels in healthy volunteers. Quantitative microbiologic determinations of *P. acnes* levels were conducted before, during and after treatment in selected subjects with high facial counts of *P. acnes*. Safety and tolerance of the test product were also assessed simultaneously.

Study Design:

A randomized trial in which two topical 4.0% water based gel formulations of coated Benzoyl Peroxide according to example 1 (BPO concentration in the both formulations was 4.4%) were examined in a panel of 16 subjects who are colonized by *P. acnes*. The design was a split-face in which every subject applied each product to one side of the face (cheek) according to a randomization schedule. The table below describes the ingredients and their concentrations (in % w/w) in each of the tested formulation.

| Ingredient | Formulation A | Formulation B |
|---|---|---|
| Water | 60.23 | 54.23 |
| Coated BPO 17.5% suspension (produced according to example #1) | 25.15 | 25.15 |
| Encapsulated Octyl Palmitate 50% suspension (produced according to U.S. Pat. No. 6,303,149) | 0 | 6 |
| Glycerin | 6 | 6 |
| Propylene Glycol | 3 | 3 |
| Sodium Hydroxide 20% | 1.75 | 1.75 |
| Citric acid 20% | 1.6 | 1.6 |
| Carbopol ultrez 10 | 0.87 | 0.87 |
| Dimethicone | 0.3 | 0.3 |
| Cetyl Alcohol | 1 | 1 |
| D.S EDTA | 0.1 | 0.1 |

Since it is known that oil may have an effect on reducing irritation, octyl palmitate was used in formulation B to evaluate whether an oil has an effect on decreasing irritation.

Treatment Plan:

Treatment was twice daily for 28 consecutive days. Approximately 0.2 ml of each test product was applied to the designated cheek area and rubbed in for about 5 seconds.

Each subject was given a sample of both test products to take home and was also given an instruction sheet on how to apply the products at home. The test product tubes were coded "R" for right cheek and "L" for the left cheek.

Evaluation of Irritancy and Facial Tolerance:

On each a.m. visit to the testing facility during weekdays, and prior to application of the test product by the technician, the cheeks were clinically evaluated by a blinded observer for any abnormal reactions including erythema, edema, scaling, rash, etc. These, if present, were documented in the case record forms using a linear scale (0 to 3) for each end-point as follows:

0=no visible abnormal reactions
1=minimal
2=moderate
3=severe

Quantitative Bacteriology:

Quantitative bacteriologic cultures were obtained from the test site (each cheek) at baseline (0) and at two and four weeks. Total densities of *P. acnes* are calculated and reported as $\log_{10}$ cfu per $cm^2$. The data was analyzed and compared by using appropriate statistical tests, such as paired t-tests.

Results:

Clinical Reactions:

There were very few clinical reactions. No skin irritation or erythema was observed. One subject (#04) reported mild burning/stinging (grade 1) on days 7, 8 and 9 only on both cheeks and minimal scaling (grade 1) on days 8 through 12 also on both cheeks after which the scaling subsided. These reactions were transient and sporadic, and did not persist despite continued product applications. These reactions developed equally to both test products. He also noted "dryness" on both cheeks. During the course of the study, subject #04 also reported visiting a tanning salon on a regular basis which may have contributed to the scaling.

Another subject (#07) developed mild (grade 1) scaling on both cheeks for five consecutive days only.

Efficacy:

The net reduction in *P. acnes* counts compared to baseline (in $\log_{10}/cm^2$) for each treatment as shown in Table 2. The mean log reduction at week 2 for "A" was 2.16 and "B" 2.4. At week 4, the mean log reduction for "A" was 2.64 and for "B" 2.94. The number of subjects achieving various degrees of *P. acnes* inhibition is summarized in Table 3. At week 2, the number of subjects achieving ≥1.0 log reduction with "A" was 14 out of 16 and for "B", 13 out of 16. By week 4, the proportion of subjects showing various degrees of inhibition was comparable for both products with "A" producing >1.0 log inhibition in 87% of the subjects, and "B" producing >1.0 log inhibition in almost 94% of the subjects. Thus, both test products produced a highly significant statistical reduction of *P. acnes* at both week 2 and week 4 (paired t-test, P<0.001).

Conclusion and Discussion:

Both formulations (A and B) produced a quick and highly significant reduction in *P. acnes*. The magnitude of the reduction is comparable to that of 5-10% formulations of uncoated benzoyl peroxide. The 5-10% uncoated BPO formulations are known to cause moderate to severe irritation in up to 25% of the users and mild irritation in up to 50% of the users. The tolerability of these formulations was excellent; only one subject had episodes of burning and stinging along with dryness/scaling on both cheeks. All other panelists showed no signs of irritation and had no neurosensory adverse symptoms. Further, the results obtained for formulation B show that the reduced side effects originate from the coating of BPO with the metal oxide layer and not from the oil (octyl palmitate), present in the formulation.

TABLE 2

*P. acnes* - Log/$cm^2$

| | Baseline | | Week 2 | | Week 4 | | Net Change from Baseline | | | |
|---|---|---|---|---|---|---|---|---|---|---|
| | | | | | | | Week 2 | | Week 4 | |
| # | A | B | A | B | A | B | A | B | A | B |
| 01 | 6.38 | 6.34 | 3.35 | 3.06 | 3.31 | 3.00 | −3.03 | −3.28 | −3.07 | −3.34 |
| 02 | 6.71 | 6.71 | 5.36 | 3.55 | 4.93 | 3.33 | −1.35 | −3.16 | −1.78 | −3.38 |
| 03 | 6.54 | 6.52 | 4.02 | 4.19 | 3.16 | 3.02 | −2.52 | −2.33 | −3.38 | −3.50 |
| 04 | 7.03 | 7.04 | 3.11 | 3.25 | 2.87 | 2.87 | −3.92 | −3.78 | −4.16 | −4.16 |
| 05 | 6.56 | 6.52 | 3.15 | 3.15 | 2.98 | 2.54 | −3.41 | −3.37 | −3.58 | −3.98 |
| 06 | 7.07 | 7.05 | 4.16 | 4.24 | 3.54 | 3.39 | −2.89 | −2.81 | −3.51 | −3.66 |
| 07 | 6.78 | 6.79 | 2.93 | 3.77 | 2.78 | 3.02 | −3.85 | −3.02 | −4.00 | −3.77 |
| 08 | 6.65 | 6.67 | 4.95 | 4.18 | 4.78 | 3.90 | −1.70 | −2.50 | −1.88 | −2.77 |
| 09 | 6.45 | 6.40 | 5.19 | 3.93 | 3.15 | 2.87 | −1.26 | −2.47 | −3.30 | −3.52 |
| 10 | 5.23 | 5.26 | 4.22 | 4.32 | 4.16 | 3.93 | −1.01 | −0.93 | −1.07 | −1.33 |
| 11 | 6.59 | 6.56 | 4.41 | 4.08 | 3.93 | 3.81 | −2.18 | −2.48 | −2.66 | −2.74 |
| 12 | 6.45 | 6.41 | 4.15 | 3.22 | 2.93 | 2.85 | −2.30 | −3.20 | −3.52 | −3.57 |
| 13 | 5.38 | 5.47 | 5.20 | 4.74 | 4.81 | 4.20 | −0.18 | −0.73 | −0.57 | −1.27 |
| 14 | 6.34 | 6.34 | 3.41 | 4.08 | 2.84 | 2.74 | −2.94 | −2.26 | −3.50 | −3.60 |
| 15 | 7.18 | 7.18 | 6.42 | 6.29 | 6.28 | 6.23 | −0.75 | −0.89 | −0.90 | −0.95 |

TABLE 2-continued

P. acnes - Log/cm²

|  | Baseline | | Week 2 | | Week 4 | | Net Change from Baseline | | | |
|  | | | | | | | Week 2 | | Week 4 | |
| # | A | B | A | B | A | B | A | B | A | B |
| --- | --- | --- | --- | --- | --- | --- | --- | --- | --- | --- |
| 16 | 7.33 | 7.33 | 6.10 | 6.15 | 5.95 | 5.81 | −1.23 | −1.18 | −1.37 | −1.51 |
| Mean | 6.54 | 6.54 | 4.38 | 4.14 | 3.90 | 3.59 | −2.16 | −2.40 | −2.64 | −2.94 |
| Std Dev | 0.56 | 0.55 | 1.07 | 0.94 | 1.14 | 1.07 | 1.14 | 0.97 | 1.19 | 1.07 |
| A vs. B T-Tests | | | | | | | | | | |
| Paired | 0.6723 | | 0.1701 | | 0.0126 | | 0.1736 | | 0.0148 | |
| Students | 0.9852 | | 0.4952 | | 0.4405 | | 0.5203 | | 0.4569 | |

A overtime (Paired T-Test) 0.0000 0.0000
B overtime (Paired T-Test) 0.0000 0.0000
A = Batch #060327
B = Batch #060328

TABLE 3

Proportion of subjects showing various degrees of P. acnes inhibition ($\log_{10}/cm^2$)

| Log reduction | A | B |
| --- | --- | --- |
| Week 2 | | |
| <0.5 | 1/16 | 0/16 |
| 0.5-0.99 | 1/16 | 3/16 |
| ≥1.0 | 14/16 | 13/16 |
| Week 4 | | |
| <0.5 | 0/16 | 0/16 |
| 0.5-0.99 | 2/16 | 1/16 |
| ≥1.0 | 14/16 | 15/16 |

Example 11: Coating of Palladium Chloride $PdCl_2$ is an inorganic very versatile catalyst for lot of organic reactions. This catalyst is used mostly as a homogenous catalyst (the catalyst is miscible in the organic medium). Coating of the immiscible powder in by silica may produce a heterogeneous catalyst. This catalyst can easily be separated from the reaction mixture and therefore may be used to catalyze reactions in aqueous medium.

A. Milling step

A PdCl2 powder is suspended in 0.5% CTAC (Polyquaternium-1) solution. The dispersion is first mixed with high shear homogenizer (Polytron PT 6100 Kinematica) with dispersing aggregates PT-DA 6045/6 in 3000 rpm for about 3 min. The dispersion then is milled in M-110Y microfluidizer processor (microfluidics) for 15 min at 15,000 psi. The ζ potential of the PdCl2 powder after milling is >0.

B. First Coating

The initial pH is adjusted to 7.4% sodium silicate solution is added to obtain pH=10, followed by acidifying the dispersion by 1 M HCl to obtain pH=2. The first step is repeated once again by using 4% sodium silicate solution and 1 M HCl. Then the pH is adjusted to 8 for an aging period.

C. Aging and Washing

Same as the former examples (aging for 48 h with pH correction to 8 and washing by filtration)

D. Addition of a 2$^{nd}$ Polycation

Solution of 0.5% on another PDAC (Polyquaternium-6) is added to the silica coated palladium chloride dispersion. The final PDAC concentration is adjusted to 0.2%. The ζ potential is >0.

E. Second Coating

Is done as paragraph B.

F. Aging and Washing

Is done as paragraph C, the final product is obtained as dispersion by suspending the wet cake with TDW G. Drying The dispersion is dried by spray dryer (Niro MOBILE MINOR) with rotary atomizer (inlet temperature 250 C, outlet temperature 80 C).

Example 12: Alumina Coating of Benzil Crystals

Sodium aluminate is polymerized to aluminum hydroxide by acidifying the solution to the isoelectric point at pH ~6.

A. Milling Step

Benzil crystals are milled in 0.3% CTAC solution by first mixing with high shear homogenizer and then milling the dispersion in high-pressure homogenizer (microfluidizer).

B. First Coating

The pH is adjusted to 4. A portion of 5% sodium aluminate solution is added to obtain pH=10 followed by acidification with 1M HCl solution to obtain pH=6 forming $Al(OH)_2$ and $Al(OH)_3$ species. The first stage is repeated by using sodium aluminate and acidifying with HCl. The pH is adjusted to 8 with 1M NaOH solution.

C. Aging and Washing

The dispersion is kept for aging for 48 h keeping the pH=8. The dispersion is separated by filtration and the wet cake is washed by RO water. The wet cake is resuspended in RO water to obtain 20% solids.

D. Polycation Addition

The pH of the dispersion is adjusted to 8. 0.6% PDAC solution is prepared and is added to the alumina coated benzil dispersion to obtain 0.2% overall PDAC concentration.

E. Second Coating

Same as step B

F. Aging and Washing

Same as step C

G. Polycation Addition

Same as step D

H. Third Coating

Same as step B

I. Aging and Final Product Preparation
   Same as step C
J. Additional Step Spray Drying of the Dispersion
   The dispersion is dried by spray dryer to obtain fine yellow powder of alumina coated benzil crystals.

Example 13: Coating Benzil Crystals with Different Metal Oxides Layers

In this case the opportunities are numerous. Mixed layers, such as silica/alumina/silica, alumina/alumina/silica, titania/alumina/silica etc, are feasible. The following example will describe mixed layers of alumina and silica. In this example there is no need to use polycation since the alumina surface at pH=4 have a positive charge making the deposition of silica on alumina surface spontaneous.
A. Milling Step
   Benzil crystals are milled in 0.3% CTAC suspension by first mixing with high shear homogenizer and then milling the dispersion in high-pressure homogenizer (microfluidizer).
B. First Coating
   The pH is adjusted to 4. A portion of 5% sodium aluminate solution is added to obtain pH=10 followed by acidification with 1M HCl solution to obtain pH=6 forming $Al(OH)_2$ and $Al(OH)_3$ species. The first stage is repeated by using sodium aluminate and acidifying with HCl. The pH is adjusted to 8 with 1M NaOH solution.
C. Aging and Washing
   The dispersion is kept for aging for 48 h keeping the pH=8. The dispersion is separated by filtration and the wet cake is washed by RO water. The wet cake is resuspended in RO water to obtain 20% solids
D. Polycation Addition
   The pH of the dispersion is adjusted to 8. 0.6% PDAC solution is prepared and is added to the alumina coated benzil dispersion to obtain 0.2% overall PDAC concentration.
E. Second Coating
   Same as step B
F. Aging and Washing
   Same as step C
G. Third Coating with Silica
   The dispersion pH is adjusted to pH 4 and $\zeta$ potential is measured to be >0. 4% sodium silicate solution is added to obtain pH=10, followed by acidifying the dispersion by 1 M HCl to obtain pH=2. The first step is repeated once again using 4% sodium silicate solution and 1 M HCl. Then the pH is adjusted to 8 for the aging period.
H. Aging and Final Product Preparation
   Same as step C

Example 14: Monocoating of Azelaic Acid

A. Milling Step
   50 g of azelaic crystals are suspended in 200 g 0.3% CTAC solution. The suspension is milled first in high shear homogenizer (polytron 6100, Kinematica. 3000 rpm, for 3 min), and then by microfluidizer for 15 min. The $\zeta$ potential of the suspension is >0.
B. Coating Step
   The dispersion is stirred rapidly with a mechanical stirrer. 15% sodium silicate solution are added to the dispersion to obtain pH=7 followed by acidification to pH=2 by adding 5N HCl solution. This step is repeated once again using the same sodium silicate and HCl solutions. The pH of the dispersion is adjusted to 7.0 by using 5N NaOH solution.
C. Aging Step
   The dispersion is kept for aging with gentle stirring for 48 h in which pH range is kept at 7.0.
D. Separation and Final Product Preparation
   The dispersion is separated by filtration. The wet cake is washed for a few times with RO water. The wet cake is resuspended in RO water to obtain 20% solids dispersion.
   The dispersion can be dried by spray dryer to obtain dry powder.

Example 15: BET Measurements of the Samples

1. Preparation of Core-Shell Particles Powders (Sample A)
   100 g of silica encapsulated paraffin oil (produced according to U.S. Pat. No. 6,303,149) were dried in an oven at 60 C. The dry powder was suspended in hexane to extract the oil from the core followed by filtration and resuspending the capsules in hexane again. After 4 cycles of extraction and washing the core material, the remaining silica was dried in oven at 60 C for two days.
2. Preparation of Silica Coated Bromobenzil Powder (Sample B)
   100 g of bromobenzil silica coated dispersion (according to example #4) were filtered in a buchner funnel. The wet cake was dried in the oven at 60 C for two days.
3. BET Measurements
   Both powders were degassed at 60 C for 30 min under high vacuum prior to the measurement. BET measurements were done in SA3100 equipment (Coulter). The surface area was calculated using multipoint adsorption isotherm. The results are given below in $m^2/g$:
   Sample A: 2.771
   Sample B: 91.725

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A process for coating an organic pharmaceutically active material in the form of a solid, water-insoluble particulate matter with a metal oxide coating, comprising:
   (a) contacting, in a medium consisting of an aqueous medium, the solid, water-insoluble organic pharmaceutically active particulate matter with a cationic additive to obtain a dispersion of said particulate matter in said aqueous medium, said particulate matter having a positive zeta potential;
   (b) adding an aqueous solution of a metal oxide salt to said dispersion of said particulate matter, under conditions wherein said metal oxide salt precipitates onto the surface of the particulate matter, and acidifying to thereby form a solid, water-insoluble particulate matter that has a metal oxide layer coated thereon; and
   (c) aging said metal oxide layer to form an aged, coated, solid, water-insoluble particulate matter having a coating thickness in the range of about 0.3-10 micron; and (d) after said aging step (c), subjecting the aged, coated, solid, water-insoluble particulate matter to one or more steps of precipitation of metal oxide salt onto the surface of the particulate matter in the presence of a cationic additive, and acidifying to thereby form a solid, water-insoluble particulate matter that has a metal oxide layer coated thereon, followed by aging treatment.

2. The process of claim 1, comprising:
(a) contacting, in a medium consisting of an aqueous medium, the solid, water-insoluble particulate matter, with a cationic additive to obtain a dispersion of said particulate matter in said aqueous medium, said particulate matter having a positive zeta potential, wherein said solid, water-insoluble particulate matter is an organic pharmaceutically active ingredient;
(b) adding an aqueous solution of a metal oxide salt to said dispersion of said particulate matter, under conditions wherein said metal oxide salt precipitates onto the surface of the particulate matter, and acidifying to thereby form solid, water-insoluble particulate matter that has a metal oxide layer coated thereon;
(c) aging said metal oxide layer to form an aged, coated, solid, water-insoluble particulate matter;
(d) contacting the aged, coated particulate matter of the immediately preceding step with a cationic additive in a medium consisting of an aqueous medium to obtain a dispersion of said aged, coated particulate matter having a positive zeta potential;
(e) adding an aqueous solution of a metal oxide salt to said dispersion obtained in the immediately preceding step, under conditions wherein said metal oxide salt precipitates onto the surface of the particulate matter, and acidifying to thereby form solid, water-insoluble particulate matter that has a metal oxide layer coated thereon; and
(f) aging said metal oxide layer formed in the immediately preceding step to form an aged, coated, solid, water-insoluble particulate matter.

3. The process of claim 2, comprising, after step (f), repeating steps (d), (e) and (f) one or two additional times.

4. The process of claim 2, wherein the cationic additive used in step (a) and the cationic additive used in step (d) are the same.

5. The process of claim 2, wherein the cationic additive used in step (a) and the cationic additive used in step (d) are different.

6. The process of claim 2, wherein said cationic additive of step (a) is a cationic surfactant selected from the group consisting of monoalkylquaternary ammonium salts, dialkyl quaternary ammonium salts, and mixtures thereof.

7. The process of claim 2, wherein said cationic additive of step (d) is a cationic polymer.

8. The process of claim 2, wherein said cationic additive of step (d) is selected from the group consisting of colloidal alumina, colloidal ceria ($CeO_2$), colloidal alumina coated silica, and mixtures thereof.

9. The process of claim 1, further comprising, after said step (c), separating the coated particulate matter from the dispersing aqueous medium and optionally rinsing and redispersing the obtained coated active ingredient in an aqueous medium.

10. The process of claim 1, wherein, in step (b) the conditions wherein said metal oxide salt precipitates onto the surface of the particulate matter are those that cause a pH of 7-11 to be yielded in the aqueous medium, and said acidifying is to an extent that yields a pH of 1-3.

11. The process of claim 1, wherein, in step (b), the conditions wherein said metal oxide salt precipitates onto the surface of the particulate matter are obtained by adjusting the pH of the dispersion obtained in (a) to a value in the range 5.5-8 and then adding the aqueous solution of the metal oxide salt.

12. The process of claim 1, wherein the aging of step (c) comprises adjusting the pH to a value in the range 6.5-9.5 and mixing for a period of at least 12 h.

13. The process of claim 1, wherein said positive zeta potential in step (a) is less than +150 mV.

14. The process of claim 1, wherein said organic pharmaceutically active material is a dermatologically active agent.

15. The process of claim 14, wherein said dermatologically active agent is selected from the group consisting of antifungal agents, antibacterial agents, antiinflammatory agents, antipuritic agents, antipsoriatic agent, anti-acne agents, and combinations of any of the above.

16. The process of claim 15, wherein said dermatologically active agent is an anti-acne agent selected from the group consisting of benzoyl peroxide, retinoid, and mixtures thereof.

17. The process of claim 16, wherein said anti-acne agent is benzoyl peroxide.

18. The process of claim 1, wherein said cationic additive is selected from the group consisting of a cationic surfactant, a cationic polymer, and mixtures thereof.

19. The process of claim 18, wherein said cationic additive is a cationic polymer selected from the group consisting of poly(ethyleneimine), poly(dimethyldiallylammonium chloride), poly(acrylamide-co-diallyl-dimethylammonium chloride), poly(allylamine hydrochloride), Chitosan, poly lysine, and mixtures thereof.

20. The process according to claim 1, further comprising, after step (c), chemically modifying the surface of the aged, coated, solid, water-insoluble particulate matter.

21. An aged, solid, water-insoluble organic pharmaceutically active particulate matter that has a metal oxide layer coated thereon, obtained by the process of claim 1.

22. A composition comprising coated particulate matter in accordance with claim 21 and a carrier.

23. The composition according to claim 22, wherein said coated particulate matter has a surface area of about 20-400 $m^2/g$, and wherein said metal oxide layer has a thickness in the range of about 0.3-10 micron.

24. The composition of claim 23, wherein the weight ratio of said metal oxide to said solid, water-insoluble particulate matter, is in the range of about 3:97 to about 50:50.

25. The composition of claim 24, wherein the weight ratio of said metal oxide to said solid, water-insoluble particulate matter, is in the range of about 10:90 to about 20:80.

26. The composition of claim 23, wherein said coated particulate matter has a diameter of about 0.5-100 micron.

27. The composition of claim 22, wherein said metal oxide is selected from the group consisting of silica, titania, alumina, ZnO, and mixtures thereof.

28. The composition of claim 22, further comprising hydrophobic groups attached to the surface of the metal oxide layer.

29. The composition of claim 28, wherein said hydrophobic groups are selected from the group consisting of alkyl silane, aryl silane, and mixtures thereof.

30. A method for treating a surface condition in a subject, comprising topically administering onto the surface a composition according to claim 22.

31. The method of claim 30, wherein said surface is skin or mucosal membrane.

32. The method of claim 31, wherein said surface condition is a disease or disorder selected from the group consisting of acne, infection, inflammation, pruritus, psoriasis, seborrhea, contact dermatitis, rosacea, and a combination thereof.

33. The method of claim 30, wherein said solid, water insoluble organic dermatologically active agent is benzoyl peroxide or retinoid.

34. The process of claim 1, wherein the metal oxide salt is a salt of a silicate, an aluminate, a titanate or a zirconate.

35. The process of claim 1, wherein said solid, water-insoluble particulate matter has a particle size of about 0.5-100 microns.

36. A composition for topical administration, comprising:
a plurality of particles, each of said particles comprising a solid, water insoluble organic dermatologically active agent, having a metal oxide layer coated on the surface of the solid, water insoluble organic dermatologically active agent, wherein said coated particles have a surface area of about 20-400 m$^2$/g and said metal oxide layer has a thickness in the range of about 0.3-10 micron; and
a carrier;
said composition having reduced side effects and at least essentially the same therapeutic effect as compared to a reference composition, the difference between said composition and the reference composition being that in the latter the active agent is not coated.

37. The composition of claim 36, wherein said dermatologically active agent is selected from the group consisting of antifungal agents, antibacterial agents, antiinflammatory agents, antipruritic agents, antpsoriatic agent, and anti-acne agents.

38. The composition of claim 37, wherein said anti-acne agent is selected from the group consisting of benzoyl peroxide, retinoid, and mixtures thereof.

39. The composition of claim 37, wherein said anti-acne agent is benzoyl peroxide and said side effects are irritation, erythema, scaling, dryness, and stinging.

40. The composition of claim 37, wherein said anti-acne agent is benzoyl peroxide.

41. The composition of claim 36, wherein and said dermatological agent is an anti-acne agent, said composition yielding a therapeutic effect manifested in a colony reduction of *P. acnes*.

42. The composition of claim 41, wherein said therapeutic effect is at least a 0.5 logarithmic colony reduction of *P. acnes* in at least 90% of the subjects treated.

43. The composition of claim 41, wherein said therapeutic effect is at least 1 logarithmic colony reduction of *P. acnes* in at least 60% of the subjects treated.

44. A method for treating a surface condition in a subject, comprising topically administering onto the surface the composition of claim 36.

45. The method of claim 44, wherein said surface is skin or mucosal membrane.

46. The method of claim 44, wherein said surface condition is a disease or disorder selected from the group consisting of acne, infection, inflammation, pruritus, psoriasis, seborrhea, contact dermatitis, rosacea, and a combination thereof.

47. The method of claim 44, wherein said solid, water insoluble particulate matter, is benzoyl peroxide or retinoid.

* * * * *